«12» United States Patent
Branco et al.

(10) Patent No.: US 8,076,102 B2
(45) Date of Patent: Dec. 13, 2011

(54) COMPOSITIONS AND METHODS FOR METABOLIC SELECTION OF TRANSFECTED CELLS

(75) Inventors: Luis Branco, Rockville, MD (US); Darryl Sampey, Littlestown, PA (US)

(73) Assignee: Biofactura, Inc., Rockville, MD (US)

( * ) Notice: Subject to any disclaimer, the term of this patent is extended or adjusted under 35 U.S.C. 154(b) by 802 days.

(21) Appl. No.: 11/914,725

(22) PCT Filed: May 18, 2006

(86) PCT No.: PCT/US2006/019344
§ 371 (c)(1),
(2), (4) Date: Nov. 16, 2007

(87) PCT Pub. No.: WO2006/125126
PCT Pub. Date: Nov. 23, 2006

(65) Prior Publication Data
US 2010/0028940 A1  Feb. 4, 2010

Related U.S. Application Data

(60) Provisional application No. 60/681,969, filed on May 18, 2005.

(51) Int. Cl.
*C12P 21/06* (2006.01)
*C07H 17/00* (2006.01)
(52) U.S. Cl. .................... 435/69.1; 435/320.1; 536/23.1
(58) Field of Classification Search .................. 436/69.1; 435/320.1, 69.1; 536/23.1
See application file for complete search history.

(56) References Cited

U.S. PATENT DOCUMENTS
5,110,737 A  5/1992  Myoken et al.

FOREIGN PATENT DOCUMENTS
WO  WO 2006099369  9/2006

OTHER PUBLICATIONS

Abbaszade et al. 1995; The mouse 3_-hydroxysteroid dehydrogenase multigene family includes two functionally distinct groups of proteins. Molecular Endocrinology 9: 1214-1222.*
Nokelainen et al. 1998; Expression cloning of a novel estrogenic mouse 17_-hydroxysteroid deyhydrogenase/17-ketosteroid reductase (m17HSD7), previously described as a prolactin receptor-associated protein (PRPA) in rat. Molecular Endocrinology. 12: 1048-1059.*
Abbaszade et al., "The Mouse 3 beta-Hydroxysteroid Dehydrogenase Multigene Family Includes Two Functionally Distinct Groups of Proteins," Molecular Endocrinology, Sep. 1995, vol. 9, pp. 1214-1222, pp. 1215 and 1216, Fig. 1, 4.
Nokelainen et al., "Expression Cloning of a Novel Estrogenic Mouse 17 beta-Hydroxysteroid Dehydrogenase/17-Ketosteroid Reductase (m17HSD7), Previously Described as a Prolactin Receptor-Associated Protein (PRAP) in Rat," Molecular Endocrinology, Jul. 1998, vol. 12, pp. 1048-1059, p. 1051, Fig. 2.
Zhou et al., "Fed-Batch Culture Recombinant NS0 Myeloma Cells with High Monoclonal Antibody Production," Biotechnol Bioeng. Sep. 1997, vol. 55(5), pp. 783-792, p. 784 (Abstract).
G. Seth et al., "17β-Hydroxysteroid Dehydrogenase Type 7 (Hsd17b7) Reverts Cholesterol Auxotrophy in NS0 Cells," Journal of Biotechnology, 2006, vol. 121, pp. 241-252.
Gen Bank: Accession No. L41519, Mus Musculus 3-Ketosteroid Reductase (HSD3b5) mRNA, 1997.
Gen Bank: Accession No. BC011464, Mus Musculus Hydroxysteroid (17-beta) Dehydrogenase 7, mRNA (cDNA Clone MGC:11432 Image:3966186), 2005.
I. Dufort et al., "Characteristics of a Highly Labile Human Type 5 17β-Hydroxysteroid Dehydrogenase," Endocrinology, 1999, vol. 140, No. 2, pp. 568-574.
Z. Marijanovic et al., "Closing the Gap: Identification of Human 3-Ketosteroid Reductase, the Last Unknown Enzyme of Mammalian Cholesterol Biosynthesis," Molecular Endocrinology, Sep. 2003, vol. 17, No. 9, pp. 1715-1725.
Jayme DW, Smith SR (2000). "Media formulation options and manufacturing process controls to safeguard against introduction of animal origin contaminants in animal cell culture.". *Cytotechnology* 33: 27-36. (Abstract).

* cited by examiner

*Primary Examiner* — Karen Carlson
(74) *Attorney, Agent, or Firm* — Womble Carlyle Sandridge & Rice, PLLC

(57) ABSTRACT

The present invention relates to novel selection marker vectors, and methods for using these vectors to generate stable gene expression systems in eukaryotic cells utilizing any enzyme useful in the eukaryotic sterol/cholesterol biosynthetic pathway, such as a 3-ketosteroid reductase, as a metabolic selection marker to select transfected cells. In one embodiment, the method comprises transfecting cells that are auxotrophic for cholesterol with a vector encoding 3-ketosteroid reductase and at least one heterologous protein, and selecting cells that have the ability to survive in medium lacking cholesterol and/or producing the heterologous protein in these cells in chemically defined and/or serum-free media.

33 Claims, 13 Drawing Sheets lanosterol (lanosta-8,24-dien-3β-ol)
does not support NS0 growth

14-demethyllanosterol
(lanosta-8,24-dien-3β,30-diol)

(lanosta-8,24-dien-3β,30-al)

4,4-dimethyl-5α-cholesta-8,14,24-triene-3β-ol

*4,4-dimethyl-5α-cholesta-8,24-diene-3β-ol*

*4α-hydroxymethyl-4β-methyl-5α-cholesta-8,24-diene-3β-ol*

*4α-formyl-4β-methyl-5α-cholesta-8,24-diene-3β-ol*

*4β-methyl-5α-cholesta-8,24-diene-3β-ol-4α-carboxylic acid*

*4-methyl-5α-cholesta-3,8,24-triene-3β-ol*

*3-oxo-4α-methyl-5α-cholesta-8,24-diene*

*4α-formyl-5α-cholesta-8,24-diene-3β-ol*

*3β-hydroxy-5α-cholesta-8,24-diene-4α-carboxylic acid*

5α-cholesta-3,8,24-triene-3β-ol

*3-ketosteroid reductase
1.1.1.270*

NS0 deficient in 3-KSR activity

3-oxo-5α-cholesta-8,24-diene

2nd cycle
NADP.H

*3-ketosteroid reductase
1.1.1.270*

NS0 deficient in 3-KSR activity delta-8,24-cholestadiene-3β-ol
3β-hydroxy-5α-cholesta-8,24-diene
zymosterol

9αH-insert
7βH+out
transposition of C=C bonds

*sterol δ8 isomerase*
*δ8-δ7 isomerase*
*5.3.3.5*

5α-cholesta-7,24-diene-3β-ol
3β-hydroxy-5α-cholesta-7,24-diene

5αH,6αH cis elimination
NADH/O2

*δ5 desaturase cytochrome b5*
*b5-reductase, Fe2+*

3β-hydroxy-cholesta-5,7,24-triene
7-dehydrodesmosterol

3β-hydroxy-cholesta-5,24-diene
24-dehydrocholesterol
desmosterol
supports NSO growth

*3β-hydroxy-cholest-5-ene*
*cholesterol*
supports NS0 growth

COMPOSITIONS AND METHODS FOR METABOLIC SELECTION OF TRANSFECTED CELLS

CROSS REFERENCE TO RELATED APPLICATIONS

This application is a national stage filing of PCT/US2006/019344, which was filed on May 18, 2006 and which claims priority to U.S. Provisional Application Ser. No. 60/681,969, filed May 18, 2005, both of which are entirely incorporated herein by reference.

FIELD OF THE INVENTION

The present invention relates to novel selection marker vectors, and methods for using these vectors to generate stable gene expression systems in eukaryotic cells.

BACKGROUND

The development of mammalian cell culture techniques has revolutionized biological research. Cell culture systems can be used to test new drugs for toxicity or efficacy at an early stage in development when human clinical testing would be high-risk; to produce complex human proteins for therapeutic applications, such as monoclonal antibodies; and as a platform for cell-based therapeutics in the context of adult and embryonic stem cell cultures. In addition, the ability to introduce heterologous recombinant DNA into cultured cell lines gives scientists a powerful adjunct tool for manipulating animal systems for experimentation.

Recently, the need to address regulatory concerns about contamination of cell lines used to express biomolecules and subsequently to manufacture therapeutic products has become more critical. The biotechnology industry as a whole is moving away from the use of FBS-supplemented media for commercial cell culturing in order to ensure that potential animal pathogens or disease-causing animal proteins are not introduced into the human population via future biologics. Serum-free media are becoming the standard protocol for culturing mammalian cells, especially those used for gene expression and protein purification within biologic product pipelines.

The NS-0 mouse myeloma cell line is commonly used in protein expression systems, such as Lonza's GS Gene Expression System (Lonza Group, Basel, Switzerland). The GS Gene Expression System exploits the inability of NS-0 cells to produce enough glutamine to survive without adding exogenous glutamine to the growth medium, by using the enzyme glutamine synthetase (GS) as a marker for cellular transfection with a plasmid vector.

NS-0 cells are also cholesterol auxotrophs, resulting in a situation where media used to support the growth of the cell line must be supplemented with both cholesterol and glutamine. Adding exogenous cholesterol to aqueous media is an intricate and time-consuming process because the lipid must be coupled to sugar moieties, such as cyclodextrins, in order to increase aqueous solubility. In addition, the coupling process is inherently unstable, resulting in cholesterol-supplemented growth media with a very short shelf-life. Further, when chemically defined, serum-free media (CD-SFM) are used instead of fetal bovine serum-supplemented media (FBS) to culture cholesterol-auxotrophic cell lines, cholesterol precipitation occurs frequently. Finally, cholesterol cannot be easily filtered through small pore sterilizing membranes, such as PES, due to its inherent affinity to such polymers, thus significantly reducing the amount of cholesterol in the final filtered medium. This issue further contributes to inconsistencies in batch to batch preparations of cholesterol supplemented media. Addition of exogenous cholesterol directly to medium without passing through a filter also increases the possibility of introducing contaminants, such as adventitious agents and/or endotoxins.

The molecular mechanism underlying the cholesterol auxotrophy of NS-0 cells has recently been identified and characterized (European Collection of Cell Cultures—ECACC, No. 85110503, Deposited by Dr J Jarvis, MRC Laboratory of Molecular Biology, Cambridge, 73B(3) Methods in Enzymology (1981). The cell line does not express the gene coding for an enzyme that catalyzes a step in the endogenous biosynthesis of cholesterol. An enzyme called 3-ketosteroid reductase (3-KSR), one member of a large family of beta-hydroxysteroid dehydrogenases, is encoded by the specific gene. The 3-KSR protein catalyzes the conversion of zymosterone into zymosterol, a precursor of cholesterol. Marijanovic et al., 17(9) Mol. Endocrinol. 1715-25 (2003).

A number of different techniques have been proposed to address the cholesterol auxotrophy of NS-0 cells with the goal of making the culturing protocol more efficient and less dependent on successful cholesterol solubility in aqueous media. One approach has been to use plant-derived or synthetic lipids instead of animal-derived cholesterol to supplement CD media. Gorfien et al., 16(5) Biotechnol. Prog. 682-7 (2000). Another approach has been to engineer NS-0 cells to overexpress 3-KSR, thereby reverting the enzymatic deficiency and allowing the cell line to be cultured without the addition of exogenous cholesterol. Seth et al., 121(2) J. Biotechnol. 241-52 (2006). Finally, researchers are investigating the molecular basis for 3-KSR gene inactivity in NS-0 cells and attempting to restore expression of the gene by demethylating a critical upstream regulatory region, which would relieve the transcriptional repression of the 3-KSR gene. Seth et al., 93(4) Biotechnol. Bioeng. 820-27 (2006).

Nevertheless, there remains a great need in the biotechnology industry for generating stable cell lines through transfection with expression vectors in chemically defined/serum-free media, which are capable of expressing heterologous molecules. Moreover, it is highly desired that the chemically defined/serum-free media is usable off-the-shelf without the need for problematic addition of exogenous cholesterol. The present invention provides an expression vector containing a gene or polynucleotide encoding an enzyme in the sterol or cholesterol biosynthetic pathway of a eukaryotic cell that imparts the ability of the cell to survive and be cultured on chemically defined and/or serum-free media. When this expression vector also comprises a gene or polynucleotide encoding a heterologous protein, polypeptide or peptide, this vector is useful as a metabolic selection marker to select the transfected cells that contain the gene encoding the heterologous protein that can be produced in chemically defined and/or serum-free media.

SUMMARY

The present invention relates to novel metabolic selection marker vectors, and methods for using these vectors to generate stable gene expression systems in eukaryotic cells.

The present invention includes a vector comprising a polynucleotide encoding an enzyme in the sterol biosynthetic pathway of a eukaryotic cell, a biologically active fragment thereof or a biologically active variant thereof and a polynucleotide encoding a heterologous polypeptide. The present invention further includes a host cell transformed with the vector.

The present invention also includes a kit comprising: a vector comprising a vector comprising a polynucleotide that encodes an enzyme in the sterol biosynthetic pathway of a eukaryotic cell, a biologically active fragment thereof or a biologically active variant thereof; and optionally one or more of: a plurality of host cells that are auxotrophic for cholesterol; chemically defined, serum-free media; growth supplements that support the growth of the plurality of host cells at low-seeding and clonal densities; and at least one protocol or written instructions to utilize the kit.

The present invention additionally includes a method of selecting cells that can survive in medium without cholesterol comprising: transfecting eukaryotic cells that are auxotrophic for cholesterol with a vector comprising a polynucleotide that encodes an enzyme in the sterol biosynthetic pathway of a eukaryotic cell, a biologically active fragment thereof or a biologically active variant thereof and optionally at least one polynucleotide that encodes a heterologous protein; and selecting cells that have the ability to survive in medium lacking cholesterol.

The present invention further comprises a method for obtaining cells that have the ability to survive in a medium lacking cholesterol and to produce a heterologous protein comprising: transfecting eukaryotic cells that are auxotrophic for cholesterol with a vector as described herein containing an enzyme, such as a 3-KSR, and at least one polynucleotide that encodes a heterologous protein; and selecting the cells that have the ability to survive in medium lacking cholesterol.

DETAILED DESCRIPTION

Figure 1A:
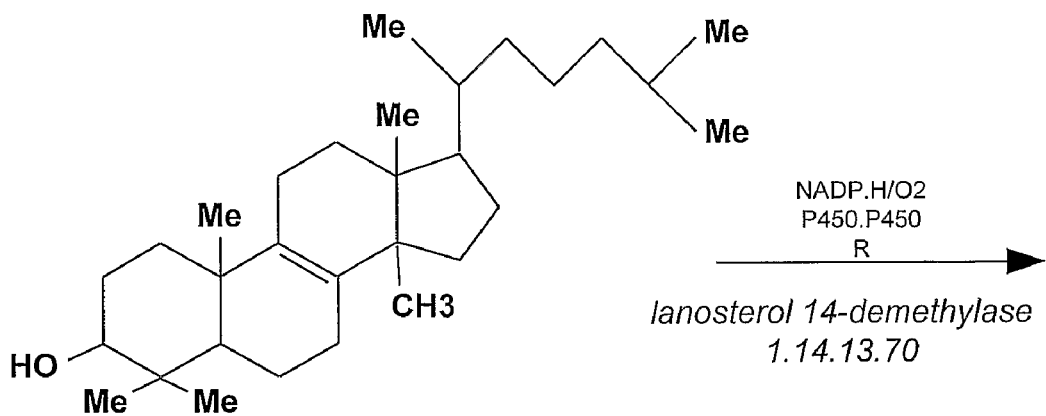
FIGS. 1A-1J shows the biochemical pathway for eukaryotic and specifically, mammalian sterol biosynthesis which is partially mediated by the product of the 3-KSR gene.
Figure 1A:
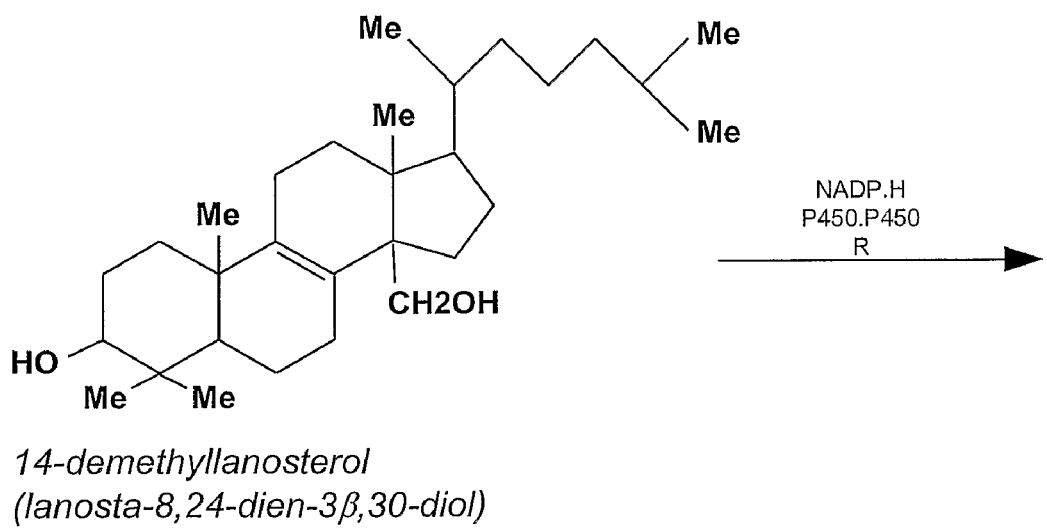
Figure 1B:
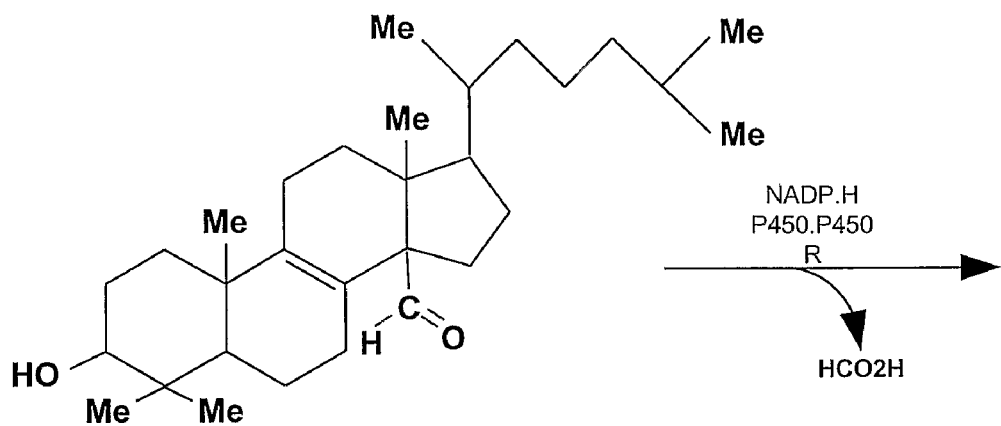
Figure 1B:
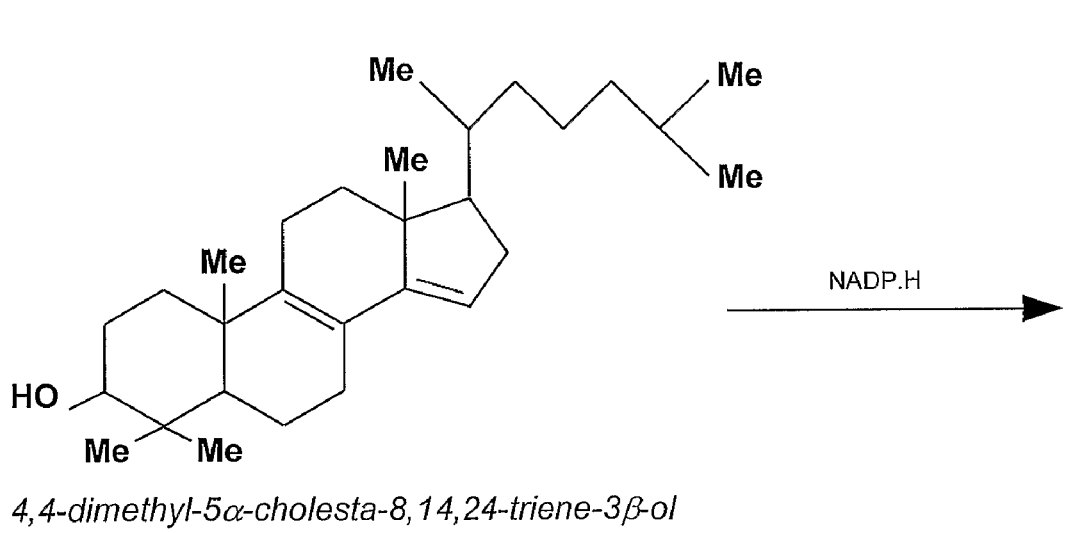
Figure 1C:
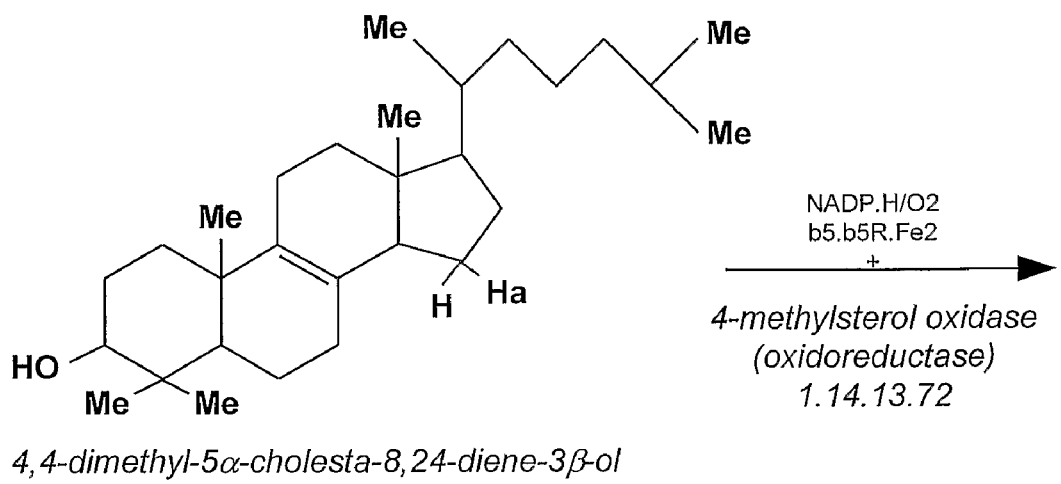
Figure 1C:
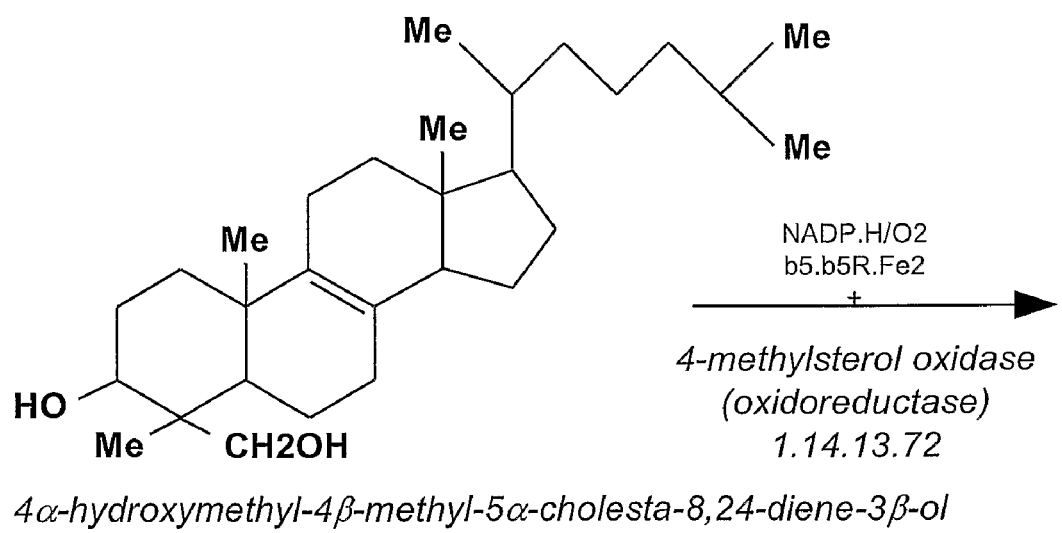
Figure 1D:
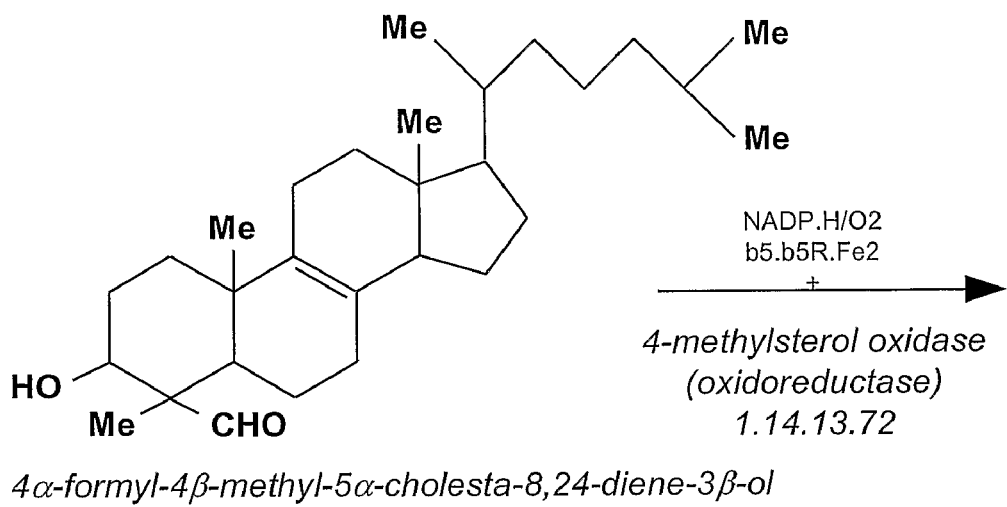
Figure 1D:
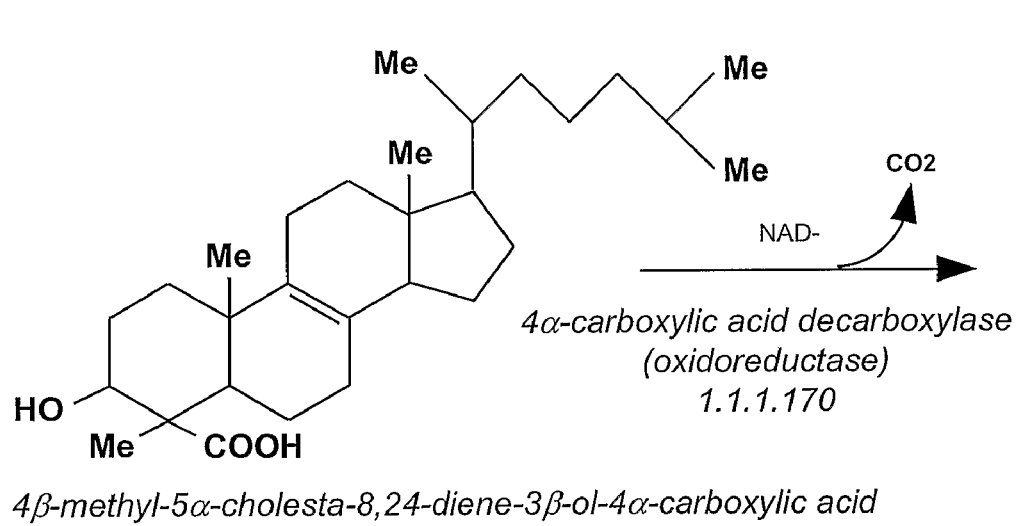
Figure 1E:
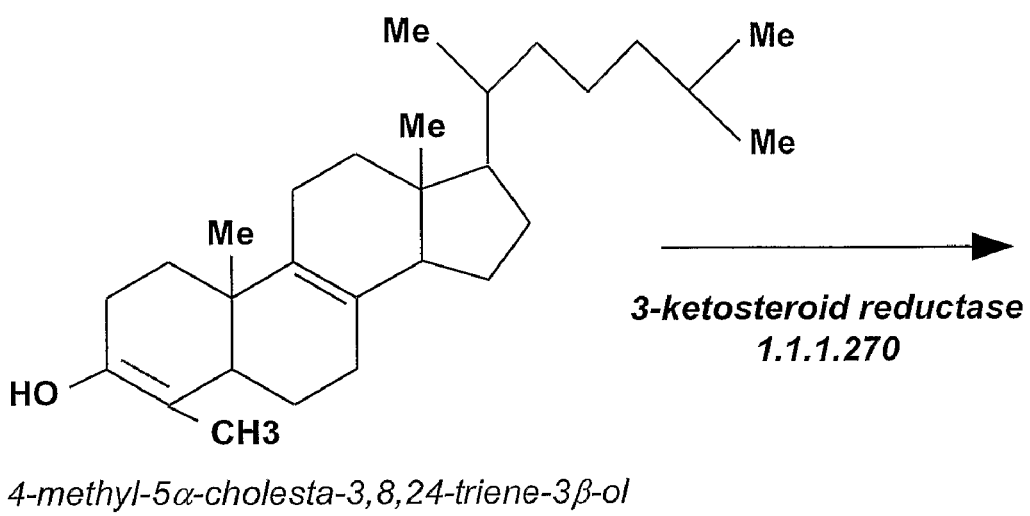
Figure 1E:
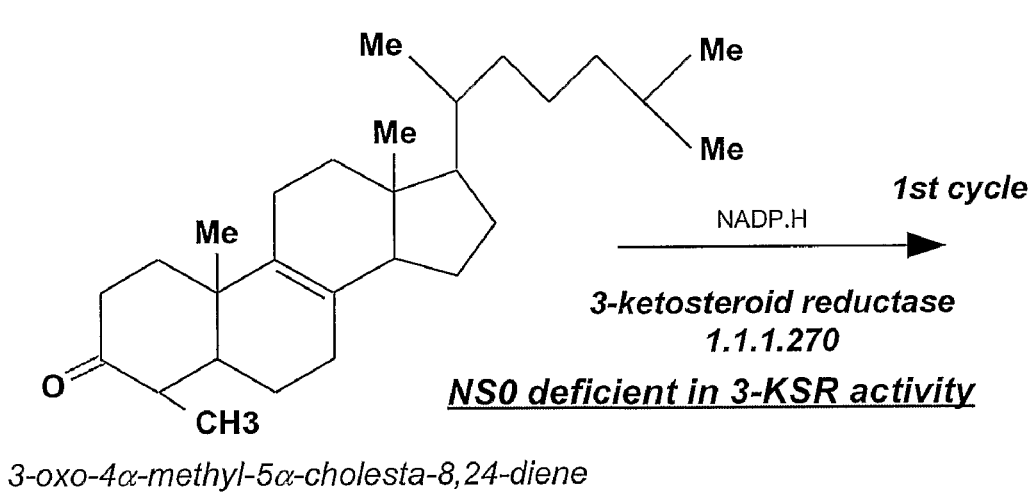
Figure 1F:
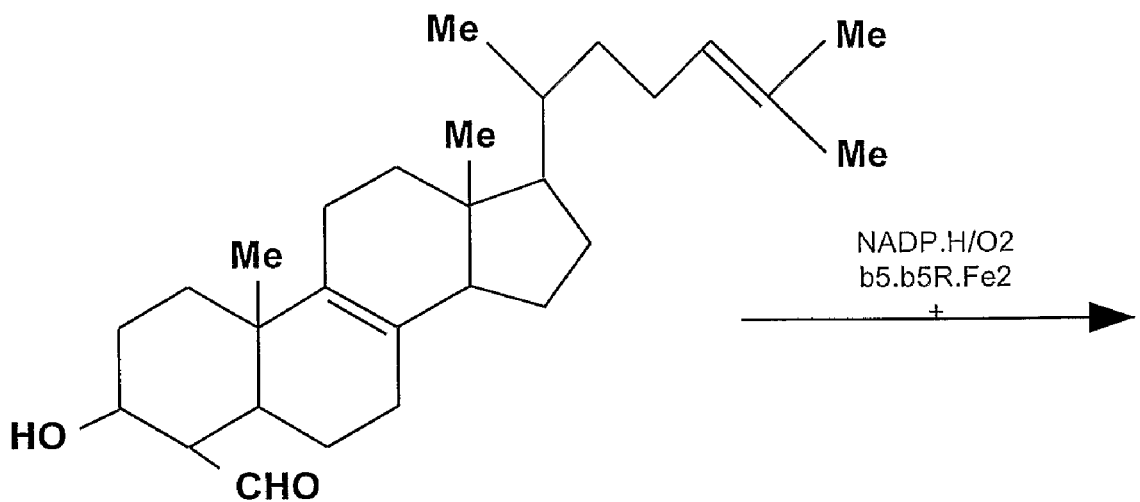
Figure 1F:
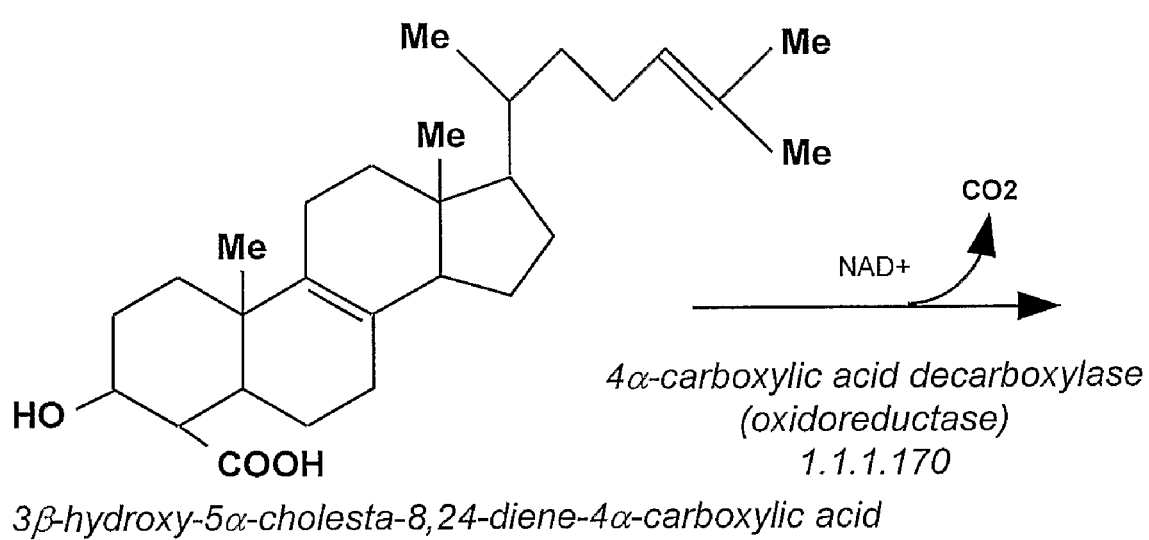
Figure 1G:
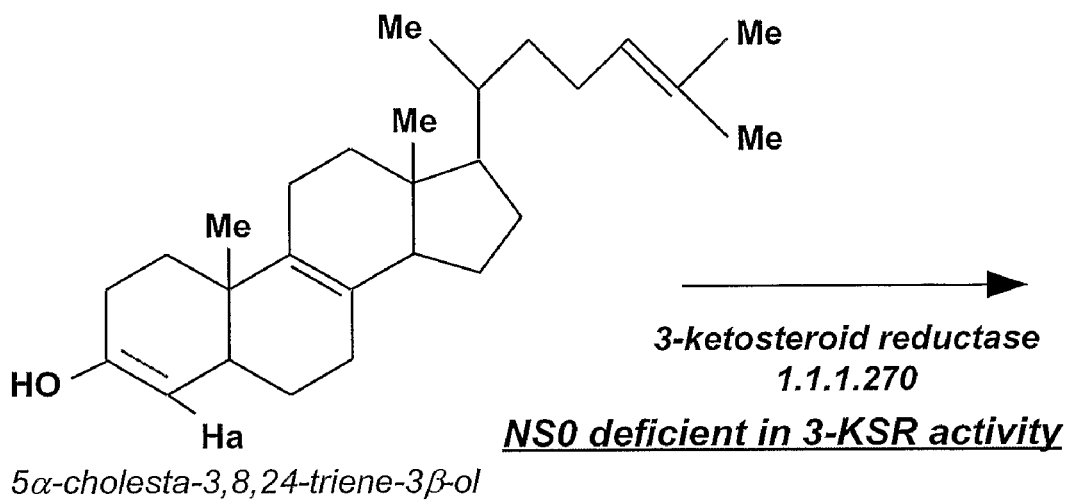
Figure 1G:
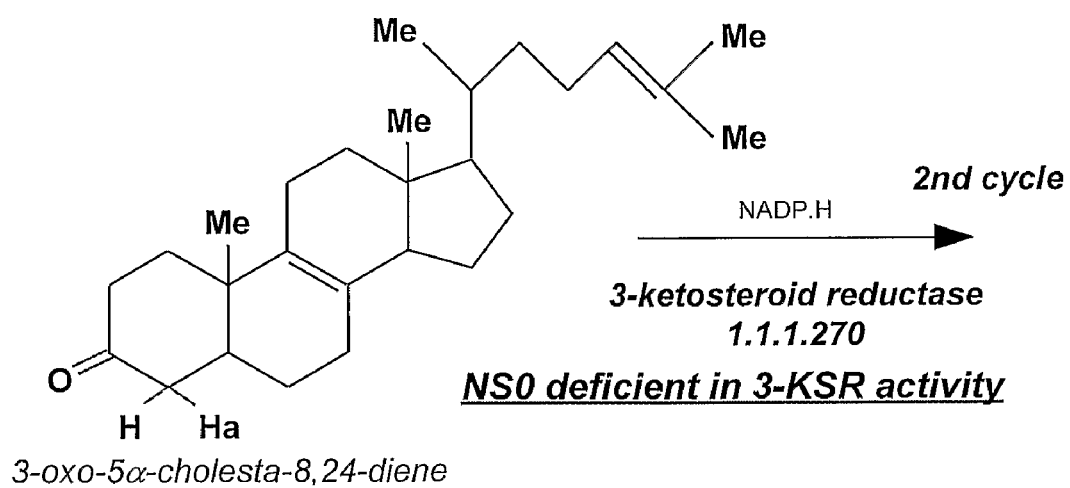
Figure 1H:
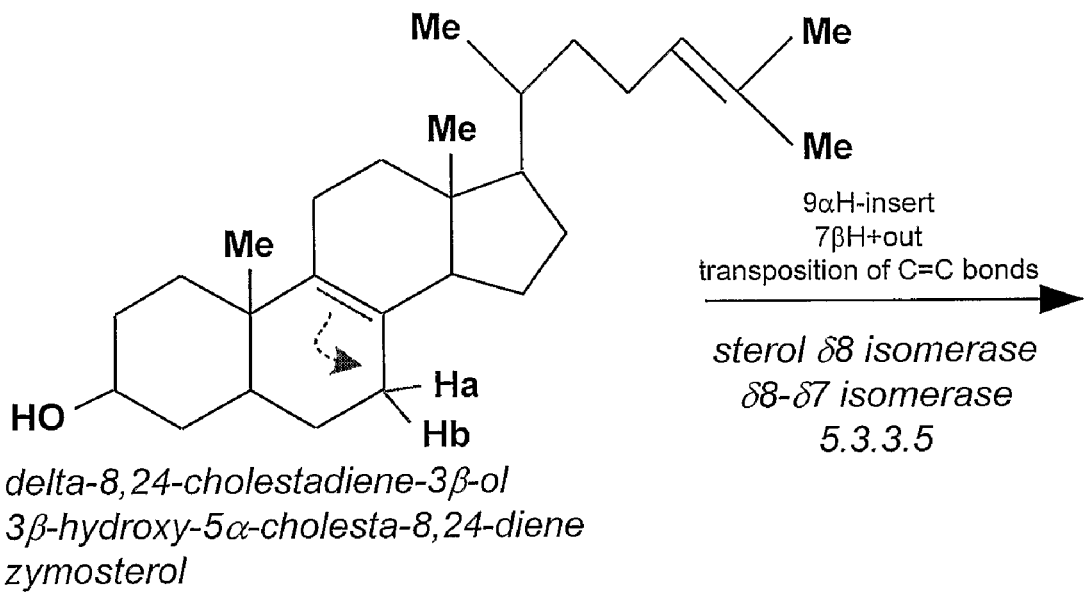
Figure 1H:
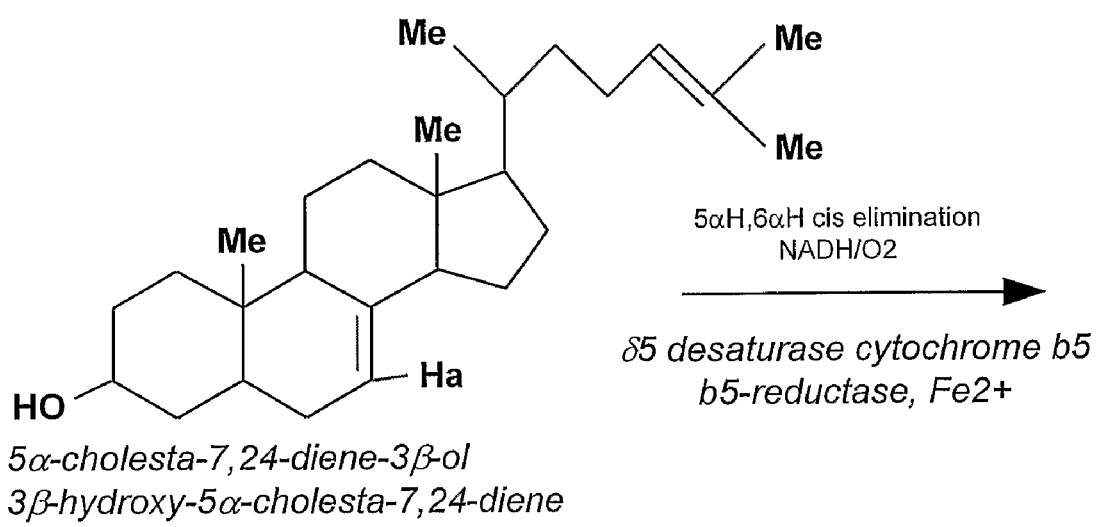
Figure 1I:
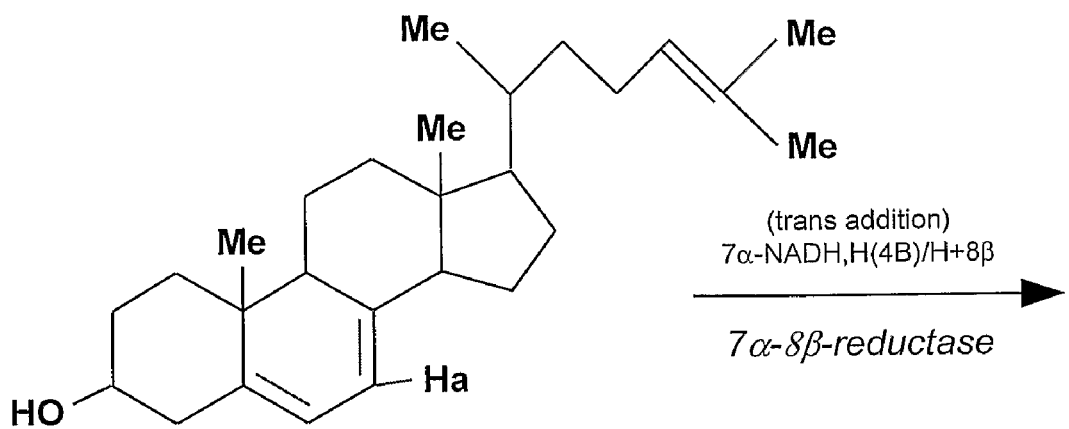
Figure 1I:
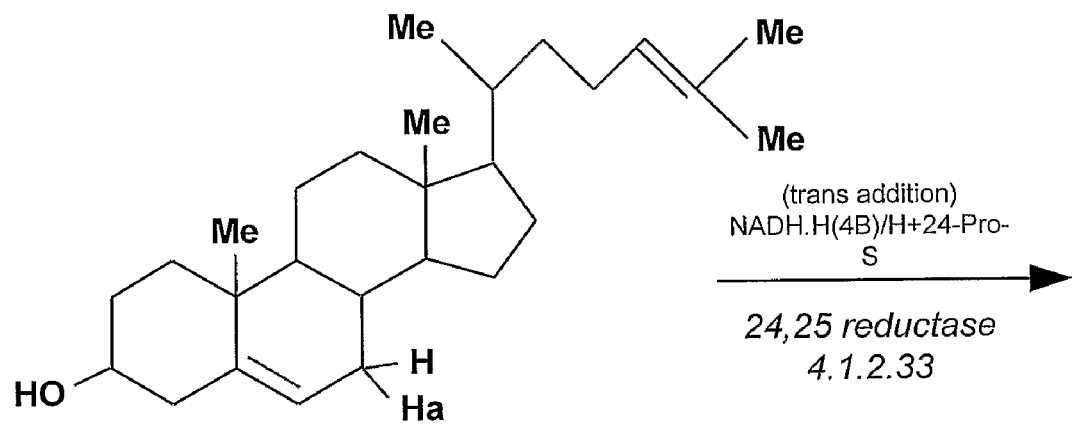
Figure 1J:
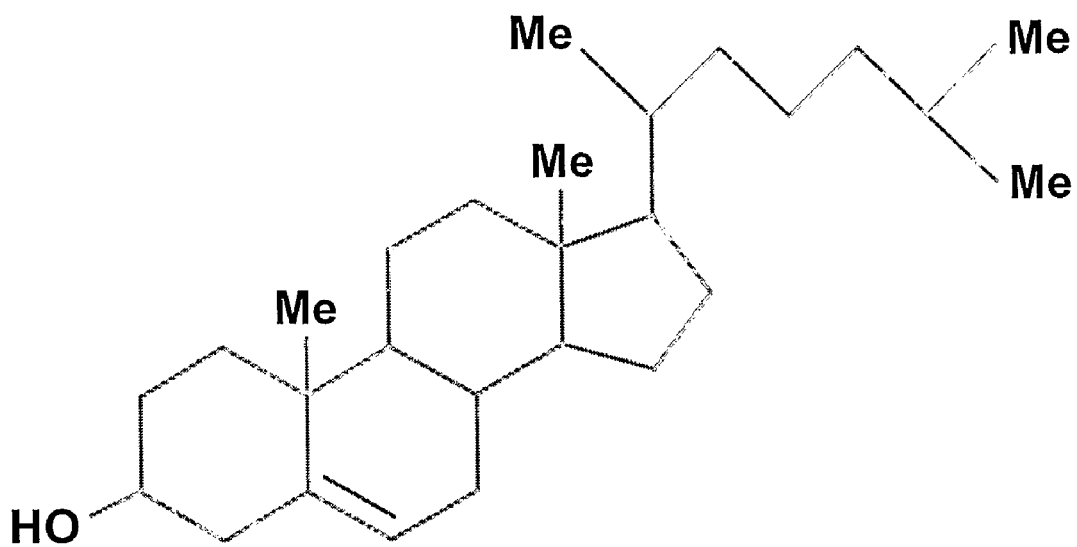

It is understood that the present invention is not limited to the particular methods and components, etc, described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "a polynucleotide" is a reference to one or more polynucleotides and includes equivalents thereof known to those skilled in the art and so forth. The term "vector" is a reference to a self-replicating DNA molecule, which also is referred to herein as a "plasmid" or a "plasmid cloning vector", which is a plasmid used in recombinant DNA experiments as an acceptor of foreign or heterologous DNA. The heterologous protein, polypeptide or peptide are intended to encompass any protein that is useful to treat conditions or diseases or as reagents.

Unless defined otherwise, all technical and scientific terms used herein have the same meanings as commonly understood by one of ordinary skill in the art to which this invention belongs. Specific methods, devices, and materials are described, although any methods and materials similar or equivalent to those described herein can be used in the practice or testing of the present invention.

The present invention provides compositions and methods useful for metabolic selection of transfected cells by utilizing an enzyme of the mammalian sterol biosynthesis pathway as a metabolic selection gene in eukaryotic cells which are deficient in the enzyme. Eukaryotic cells with these properties are useful for the production of a heterologous molecule, such as a peptide, a polypeptide, a protein or another molecule that is not normally produced by the cell. Specifically, the present invention utilizes 3-ketosteroid reductase (3-KSR) as a metabolic selection gene in the generation of eukaryotic cell lines which are deficient in 3-KSR for the production of a heterologous molecule such as a peptide, a polypeptide or a protein in medium which lacks exogenous cholesterol or any precursors of cholesterol downstream of 3-KSR in the eukaryotic cholesterol biosynthetic pathway. See FIG. 1, which presents the biochemical pathway for mammalian sterol biosynthesis which is partially mediated by 3-KSR.

More specifically, the present invention provides polynucleotides and polypeptides encoding an enzyme in the mammalian sterol biosynthesis pathway as provided in FIG. 1, where such enzyme, for example is 3-KSR, vectors for expressing the enzyme, such as 3-KSR, cell lines that are deficient in the enzyme, such as 3-KSR, cell culture media and growth supplements for use in the transfection process, and kits for commercial exploitation of the present invention.

The present invention includes a vector comprising a polynucleotide encoding an enzyme in the sterol biosynthetic pathway of a eukaryotic cell, a biologically active fragment thereof or a biologically active variant thereof and a polynucleotide encoding a heterologous polypeptide. The enzyme in this vector more specifically comprises a 3-ketosteroid reductase (3-KSR), and more specifically a murine 3-KSR. Specific representative polynucleotides encoding a 3-KSR comprises SEQ ID NO: 1 which encodes the amino acid sequence represented by SEQ ID NO:3 and comprises SEQ ID NO: 2 which encodes the amino acid sequence represented by SEQ ID NO:4.

The vector as described above is preferably a recombinant DNA expression vector, which optionally further comprises at least a first transcription unit for a product gene which transcription unit is under control of the human cytomegalovirus promoter. Details of other units and elements in the expression vector are described in detail herein.

The present invention further includes a host cell transformed with the vector as described above. The host cell is a eukaryotic cell, which is known to persons skilled in the art to include the Protoctista, the Fungi, the Animalia, and the Plantae. Therefore, fungi, plant and mammalian cells are intended to be encompassed by the present invention as appropriate host cells. The host cell preferably is auxotrophic for cholesterol. Specific host cells that are useful in the present invention are NS-0, NS-1, and CHO-215 cells, and more specifically an NS-0 mouse myeloma cell.

The present invention also includes a kit comprising: a vector comprising a vector comprising a polynucleotide that encodes an enzyme in the sterol biosynthetic pathway of a eukaryotic cell, a biologically active fragment thereof or a biologically active variant thereof; and optionally one or more of: a plurality of host cells that are auxotrophic for cholesterol; chemically defined, serum-free media; growth supplements that support the growth of the plurality of host cells at low-seeding and clonal densities; and at least one protocol or written instructions to utilize the kit. As noted above, the enzyme preferably is a 3-KSR, and more preferably a murine 3-KSR with the vector containing for example, useful polynucleotides encoding the enzyme comprising SEQ ID NO: 1 and SEQ ID NO: 2. These polynucleotides encode the amino acid sequence of the enzymes comprising SEQ ID NO:3 and SEQ ID NO:4, respectively. The vector in the kit is preferably a recombinant DNA expression vector, which optionally further comprises at least a first transcription unit for a product gene which transcription unit is under control of the human cytomegalovirus promoter.

The host cells in the kit are preferably NS-0, NS-1, and CHO-215 and more preferably an NS-0 mouse myeloma cell that are adapted to grow on chemically defined, serum-free medium and/or on chemically defined medium.

The kit further may optionally contain growth supplements which comprise at least one of fatty acid-free BSA, recombinant human interleukin-t (rhIL-6), recombinant human insulin, sodium selenite, sodium pyruvate, and ethanolamine. More preferably the growth supplements comprise final concentrations in selection medium of about 0.1% to about 5% fatty acid-free BSA, about 1 ng/mL to about 9 ng/mL rhIL-6, about 5 mg/mL to about 15 mg/L recombinant human insulin, about 5 µg/L to about 8 µg/L sodium selenite, about 0.01 g/L to about 0.3 g/L sodium pyruvate, and about 0.5 mg/L to about 3.5 mg/L ethanolamine. More preferably, the growth supplements comprise final concentrations in selection medium of about 1% fatty acid-free BSA, about 5 ng/mL rhIL-6, about 10 mg/L recombinant human insulin, about 6.7 µg/L sodium selenite, about 0.11 g/L sodium pyruvate, and about 2.0 mg/L mg/L ethanolamine.

The invention further includes a composition of cell culture supplements comprising final concentrations in selection medium of about 0.1% to about 5% fatty acid-free BSA, about 1 ng/mL to about 9 ng/mL rhIL-6, about 5 mg/mL to about 15 mg/L recombinant human insulin, about 5 µg/L to about 8 µg/L sodium selenite, about 0.01 g/L to about 0.3 g/L sodium pyruvate, and about 0.5 mg/L to about 3.5 mg/L ethanolamine. Additionally, the invention also includes a composition of cell culture supplements comprising final concentrations in selection medium of about 1% fatty acid-free BSA, about 5 ng/mL rhIL-6, about 10 mg/L recombinant human insulin, about 6.7 µg/L sodium selenite, about 0.11 g/L sodium pyruvate, and about 2.0 mg/L mg/L ethanolamine.

The present invention additionally includes a method of selecting cells that can survive in medium without cholesterol comprising: transfecting eukaryotic cells that are auxotrophic for cholesterol with a vector comprising a polynucleotide that encodes an enzyme in the sterol biosynthetic pathway of a eukaryotic cell, a biologically active fragment thereof or a biologically active variant thereof and optionally at least one polynucleotide that encodes a heterologous protein; and selecting cells that have the ability to survive in medium lacking cholesterol. Preferable host cells are NS-0, NS-1, and CHO-215, and preferably the cells are NS-0 mouse myeloma cells and the medium is chemically defined and serum-free or chemically defined. The enzyme useful in this method comprises a 3-KSR.

The present invention further comprises a method for obtaining cells that have the ability to survive in a medium lacking cholesterol and to produce a heterologous protein comprising: transfecting eukaryotic cells that are auxotrophic for cholesterol with a vector as described herein containing an enzyme, such as a 3-KSR, and at least one polynucleotide that encodes a heterologous protein; and selecting the cells that have the ability to survive in medium lacking cholesterol. As previously described, the cells are auxotrophic for cholesterol, and preferably are NS-0, NS-1, and CHO-215, and more preferably are NS-0 mouse myeloma cells, which can be cultured in a medium that is chemically defined and serum-free or chemically defined.

The present invention further includes a method for producing a heterologous protein in the cell cultures system described herein comprising: transfecting eukaryotic cells that are auxotrophic for cholesterol with a vector comprising a polynucleotide that encodes an enzyme in the sterol biosynthetic pathway of a eukaryotic cell, a biologically active fragment thereof or a biologically active variant thereof; and at least one polynucleotide that encodes a heterologous protein; and culturing the cells under conditions to produce the heterologous protein. The method further comprises obtaining the heterologous protein from the cell culture by isolating, separation or purification techniques known to persons skilled in the art. The cells are auxotrophic for cholesterol, and preferably are NS-0, NS-1, and CHO-215, and more preferably are NS-0 mouse myeloma cells that can be cultured on medium that is chemically defined and serum-free or chemically defined.

The present invention further includes more specifically a method of expressing a heterologous protein comprising culturing a cell transfected with a vector comprising a sequence encoding 3-ketosteroid reductase and at least one heterologous protein in the absence of cholesterol under conditions to produce the heterologous protein wherein the preferred cells and the medium are described above.

I. 3-Ketosteroid Reductases

The present invention utilizes any eukaryotic 3-KSR as a metabolic selection gene for the production of heterologous proteins. In one embodiment, a murine 3-KSR may be used, specifically, 3β-hydroxysteroid:NADP$^+$3-oxireductase, also known as HSD3β5 (NCBI Nucleotide Accession No. L41519) with a nucleotide sequence as follows: (SEQ ID NO: 1):

```
ATGCCTGGAT GGAGCTGCCT GGTGACAGGA GCAGGAGGGT

TTCTTGGCCA GAGGATTGTC CGAATGTTGG TGCAGGAGGA

AGAGTTGCAG GAGATCAGAG CCCTGTTCAG GACCTTCGGT

CGAAAACATG AAGAGGAATT GTCCAAGCTG CAGACAAAGG

CCAAGGTGAG AGTACTGAAG GGAGACATTC TGGATGCCCA

ATGCCTGAAG AGAGCCTGCC AGGGCATGTC TGCTGTCATC

CACACCGCTG CTGCTATTGA CCCCCGTGGT GCCGCTTCCA

GACAGACCAT CCTAGATGTC AATCTGAAAG GTACTCAGCT

CCTACTGGAT GCTTGTGTGG AAGCCAGTGT GCCAACATTC

ATCTACAGCA GTCAGTGCT TGTGGCTGGA CCAAATTCCT

ACAAGGAGAT CATCCTGAAT GCCCATGAGG AAGAGCATCA

TGAAAGCACA TGGCCTAACC CATACCCATA CAGCAAAAGG

ATGGCTGAGA AGGCAGTGCT GGCAACAAAT GGGAGACTCC
```

```
TGAAAAATGG TGGCACTTTG CATACTTGTG CCTTAAGACT

CCCTTTCATC TATGGGGAAG AATGCCAAGT CACTTCAACC

ACTGTGAAAA CAGCACTGAA GAACAACAGC ATAATTAAGA

AAAATGCCAC ATTCTCCATC GCCAACCCAG TGTATGTGGG

CAATGCAGCC TGGGCTCACA TTCTGGCTGC CAGGAGCCTA

CAGGACCCCA AGAAGTCCCC AAGCATCCAA GGACAGTTCT

ATTACATCTC TGATAACACC CCTCACCAAA GCTATGATGA

TTTAAATTAC ACCCTGAGCA AGGAGTGGGG CCTCTGCCTT

GATTCTGGCT GGAGGCTTCC TCTGTCCCTG CTTTACTGGC

TTGCCTTCCT GCTGGAAACT GTGAGCTTCC TGCTACGTCC

AGTTTACAAC TATAGGCCAC CCTTTACCCG CCTCTTGATC

ACAGTGCTAA ATAGCGTGTT TACCATTTCC TATAAGAAAG

CTCAGCGCGA TCTAGGCTAT CAGCCACTTG TCAGCTGGGA

GGAAGCCAAG CAAAAAACCT CAGAGTGGAT TGGAACACTA

GTGAAGCAGC ACAGGGAGAC ACTACACAAA AAGTCACAGT

GA
```

SEQ ID NO: 1 encodes a specific 3-KSR that has the amino acid sequence as follows:

```
Murine HSD3b5 amino acid sequence (SEQ ID NO: 3):
MPGWSCLVTGAGGFLGQRIVRMLVQEEELQEIRALFRTFGRKEEELSKLQ

TKAKVRVLKGDILDAQCLKRACQGMSAVIHTAAAIDPRGAASRQTILDVN

LKGTQLLLDACVEASVPTFIYSSSVLVAGPNSYKEIILNAHEEEHHESTW

PNPYPYSKRMAEKAVLATNGRLLKNGGTLHTCALRLPFIYGEECQVTSTT

VKTALKNNSIIKKNATFSIANPVYVGNAAWAHILAARSLQDPKKSPSIQG

QFYYISDNTPHQSYDDLNYTLSKEWGLCLDSGWRLPLSLLYWLAFLLETV

SFLLRPVYNYRPPFTRLLITVLNSVFTISYKKAQRDLGYQPLVSWEEAKQ

KTSEWIGTLVKQHRETLHKKSQ*
```

Additionally, other functional enzymes are encoded by genes including, but not limited to, 17β-hydroxysteroid dehydrogenase type 7 (Hsd17b7), 3β-hydroxy-delta(5)-steroid dehydrogenase (Hsd3β5), rat 3β-Hsd III, mouse 3β-Hsd IV, mouse 3β-Hsd V and hamster 3β-Hsd III, which are known to function exclusively as 3-ketosteroid reductases. Specifically, a polynucleotide comprising SEQ ID NO: 2, also known as hydroxysteroid (17-beta) dehydrogenase 7 (Nucleotide Accession No. NCBI: BC011464) which contains the following murine HSD17b7 nucleotide sequence which is as follows:

```
ATGCGGAAGG TGGTTTTGAT CACCGGGGCG AGCAGTGGCA

TTGGGCTAGC CCTTTGCGGT CGACTGCTGG CAGAAGACGA

TGACCTCCAC CTGTGTTTGG CGTGTAGGAA CCTGAGCAAA

GCAAGAGCTG TTCGAGATAC CCTGCTGGCC TCTCACCCCT

CCGCCGAAGT CAGCATCGTG CAGATGGATG TCAGCAGCCT

GCAGTCGGTG GTCCGGGGTG CAGAGGAAGT CAAGCAAAAG

TTTCAAAGAT TAGACTACTT ATATCTGAAT GCTGGAATCC

TGCCTAATCC ACAATTCAAC CTCAAGGCAT TTTTCTGCGG

CATCTTTTCA AGAAATGTGA TTCATATGTT CACCACAGCG

GAAGGAATTT TGACCCAGAA TGACTCGGTC ACTGCCGACG

GGTTGCAGGA GGTGTTTGAA ACCAATCTCT TTGGCCACTT

TATTCTGATT CGGGAACTGG AACCACTTCT CTGCCATGCG

GACAACCCCT CTCAGCTCAT CTGGACGTCC TCTCGCAATG

CAAAGAAGGC TAACTTCAGC CTGGAGGACA TCCAGCACTC

CAAAGGCCCG GAACCCTACA GCTCTTCCAA ATATGCTACC

GACCTCCTGA ATGTGGCTTT GAACAGGAAT TTCAACCAGA

AGGGTCTGTA TTCCAGTGTG ATGTGCCCAG GCGTCGTGAT

GACCAATATG ACGTATGGAA TTTTGCCTCC CTTTATCTGG

ACGTTGCTCC TACCCATAAT GTGGCTCCTT CGCTTTTTTG

TAAATGCGCT CACTGTGACA CCGTACAACG GAGCAGAGGC

CCTGGTGTGG CTCTTCCACC AAAAACCGGA GTCTCTTAAT

CCTCTGACCA AATACGCGAG CGCCACCTCG GGATTTGGGA

CTAATTACGT CACGGGCCAA AAGATGGACA TAGATGAAGA

CACTGCTGAA AAATTCTATG AGGTCTTACT GGAGCTGGAA

AAGCGTGTCA GGACCACCGT TCAGAAATCG GATCACCCGA

GCTGA
```

SEQ ID NO:2 encodes a specific 3-KSR that has the amino acid sequence as follows: Murine HSD17b7 a.a. sequence (SEQ ID NO:4):

```
MRKVVLITGASSGIGLALCGRLLAEDDDLHLCLACRNLSKARAVRDTLLA

SHPSAEVSIVQMDVSSLQSVVRGAEEVKQKFQRLDYLYLNAGILPNPQFN

LKAFFCGIFSRNVIHMFTTAEGILTQNDSVTADGLQEVFETNLFGHFILI

RELEPLLCHADNPSQLIWTSSRNAKKANFSLEDIQHSKGPEPYSSSKYAT

DLLNVALNRNFNQKGLYSSVMCPGVVMTNMTYGILPPFIWTLLLPIMWLL

RFFVNALTVTPYNGAEALVWLFHQKPESLNPLTKYASATSGFGTNYVTGQ

KMDIDEDTAEKFYEVLLELEKRVRTTVQKSDHPS*
```

In another embodiment, any enzyme, for example such as 3-KSR that facilitates enzymatic conversion of the following precursors in the first and second cycles of mammalian sterol biosynthesis as depicted in FIG. 1 may be used:

4-methyl-5α-cholesta-3,8,24-triene-3β-ol→3-KSR→3-oxo-4α-methyl-5α-cholesta-8,24-diene→3-KSR→3β-hydroxy-4α-methyl-5α-cholesta-8,24-diene ($1^{st}$ cycle)

5α-cholesta-3,8,24-triene-3β-ol→3-KSR→3-oxo-5α-cholesta-8,24-diene→3-KSR→delta-8,24-cholestadiene-3β-ol (3β-hydroxy-5α-cholesta-8,24-diene; zymosterol) ($2^{nd}$ cycle)

Other specific examples of 3-KSRs that may be used in the present invention include other murine 3-KSRs (Accession Nos. NM_00295, NM_010476, and BC_012715), bovine (Accession No. XM_591611), human (Accession No. NM_016371).

A. 3-KSR Polynucleotides, Fragments and Variants Thereof

The present invention relates to polynucleotides encoding any 3-KSR. The scope of the invention with respect to polynucleotides encoding 3-KSR includes, but is not limited to, polynucleotides having a sequence set forth in any one of the polynucleotide sequences provided herein; polynucleotides obtained from the biological materials described herein or other biological sources (for example, murine or human sources) by hybridization under stringent conditions (particularly conditions of high stringency); genes corresponding to the provided polynucleotides; variants of the provided polynucleotides and their corresponding genes, particularly those variants that retain a biological activity of the encoded gene product (e.g., a biological activity ascribed to a gene product corresponding to the provided polynucleotides as a result of the assignment of the gene product to a protein family and/or protein families and/or identification of a functional domain present in the gene product). Other 3-KSR polynucleotide compositions contemplated by and within the scope of the present invention will be readily apparent to one of ordinary skill in the art when provided with the present disclosure. As used herein, the terms "polynucleotide" and "nucleic acid" are not intended to be limiting as to the length or structure of the polynucleotide unless specifically indicated.

The 3-KSR polynucleotides may comprise a sequence set forth in any one of the polynucleotide sequences provided herein. The 3-KSR polynucleotides of the present invention also include polynucleotides having sequence similarity or sequence identity with native 3-KSR DNA. This includes associated 5' and 3' untranslated sequences, promoter and enhancer sequences. 3-KSR polynucleotides having sequence similarity may be detected by hybridization under low stringency conditions, for example, at 50° C. and 10×SSC (0.9 M saline/0.09 M sodium citrate) and remain bound when subjected to washing at 55° C. in 1×SSC. Sequence identity may be determined by hybridization under stringent conditions, for example, at 50° C. or higher and 0.1×SSC (9 mM saline/0.9 mM sodium citrate). Of course, hybridization methods and conditions are well known in the art and all alternative methods and conditions may be used to identify additional 3-KSR polynucleotides.

The 3-KSR polynucleotides of the present invention also include naturally occurring variants of the 3-KSR nucleotide sequences (e.g., degenerate variants, allelic variants, etc.). Variants of the 3-KSR polynucleotides of the present invention are identified by hybridization of putative variants with nucleotide sequences disclosed herein, preferably by hybridization under stringent conditions. For example, by using appropriate wash conditions, variants of the 3-KSR polynucleotides described herein can be identified where the allelic variant exhibits at most about 25-30% base pair (bp) mismatches relative to the selected polynucleotide probe. In general, allelic variants contain about 15-25% bp mismatches, and can contain as little as even 5-15%, or 2-5%, or 1-2% bp mismatches, as well as a single bp mismatch.

The present invention also encompasses homologs corresponding to the 3-KSR polynucleotide sequences provided herein, where the source of homologous genes can be any mammalian species, e.g., primate species, particularly human; rodents, such as rats; canines, felines, bovines, ovines, equines, yeast, nematodes, etc. Between mammalian species, e.g., human and mouse, homologs generally have substantial sequence similarity to the gene or portion thereof, e.g., at least 75% sequence identity, usually at least 90%, more usually at least 95%, 96%, 97%, 98% or 99% between nucleotide sequences. Sequence similarity may be calculated based on a reference sequence, which may be a subset of a larger 3-KSR sequence, e.g., as a conserved motif, part of coding region, flanking region, etc. A reference sequence will usually be at least about 18 contiguous nt long, more usually at least about 30 nt long, and may extend to the complete 3-KSR sequence that is being compared. Algorithms for sequence analysis are known in the art, such as gapped BLAST, described in Altschul, et al., 25 NUCLEIC ACIDS RES. 3389-3402 (1997).

In general, variants of the 3-KSR polynucleotides described herein have a sequence identity greater than at least about 65%, at least about 75%, at least about 85%, and can be greater than at least about 90%, 95%, 96%, 98%, 99% or more as determined using conventional methods such as the Smith-Waterman homology search algorithm as implemented in MPSRCH program (Accelrys, Inc., San Diego, Calif.). For example, global DNA sequence identity may be greater than 65% as determined by the Smith-Waterman homology search algorithm using an affine gap search with the following search parameters: gap open penalty, 12; and gap extension penalty, 1.

The 3-KSR polynucleotides of the present invention may be cDNAs or genomic DNAs, as well as truncated versions or fragments thereof, particularly fragments that encode a biologically active or rescuable 3-KSR gene product that is functional in the eukaryotic cells into which it is transfect to allow the cells to grow on cholesterol free media. cDNAs include all nucleic acids that share the arrangement of sequence elements found in native mature mRNA species, where sequence elements are exons and 3' and 5' non-coding regions. Normally, mRNA species have contiguous exons, with the intervening introns, when present, being removed by nuclear RNA splicing, to create a continuous open reading frame encoding a polypeptide. mRNA species can also exist with both exons and introns, where the introns may be removed by alternative splicing.

A 3-KSR genomic sequence may comprise the nucleic acid present between the initiation codon and the stop codon, as defined in the listed sequences, including all of the introns that are normally present in a native chromosome. It can further include the 5' and 3' untranslated regions found in the mature mRNA. The genomic sequence can further include specific transcriptional and translational regulatory sequences, such as promoters, enhancers, etc., including about 1 kb, but possibly more, of flanking genomic DNA at either the 5' and 3' end of the transcribed region.

B. 3-KSR Polypeptides, Fragments and Variants Thereof

The 3-KSR polypeptides of the present invention include those encoded by the disclosed 3-KSR polynucleotides, fragments, and variants thereof including, for example, nucleic acids that, by virtue of the degeneracy of the genetic code, are not identical in sequence to the disclosed 3-KSR polynucleotides.

A 3-KSR polypeptide refers to both the full length polypeptide encoded by the recited polynucleotide, the polypeptide encoded by the gene represented by the recited polynucleotide, as well as portions or fragments thereof. 3-KSR polypeptides also include variants of the naturally occurring proteins, where such variants are homologous or substantially similar to naturally occurring 3-KSR proteins, and can be of an origin of the same or different species as the naturally occurring 3-KSR proteins (e.g., human, murine, or some other species that naturally expresses the recited polypeptide, usually a mammalian species). In general, variant 3-KSR polypeptides have a sequence that has at least about 80%, usually at least about 90%, and more usually at least about 95% sequence identity or higher, i.e., 96%, 97%, 98% or 99% sequence identity with a 3-KSR polypeptide described herein, as measured, for example, by BLAST 2.0 using the parameters described above. The variant 3-KSR polypeptides may be naturally or non-naturally post-translationally modified, i.e., the polypeptide has a post-translational modification pattern that differs from any predicted or experimentally characterized post-translation modification of the naturally occurring 3-KSR protein.

The present invention also encompasses homologs of 3-KSR polypeptides (or fragments thereof) where the homologs are isolated from any species, usually mammalian species, e.g., rodents, such as mice, rats; domestic animals, e.g., horse, cow, dog, cat; and humans. Homologs may have at least about 35%, usually at least about 40% and more usually at least about 60% amino acid sequence identity to a particular 3-KSR protein described herein, where sequence identity is determined using the BLAST 2.0 algorithm, for example, with the parameters described above.

Also within the scope of the present invention are polypeptide variants including mutants, fragments, and fusions. Mutants may include amino acid substitutions, additions or deletions. The amino acid substitutions can be conservative amino acid substitutions or substitutions to eliminate non-essential amino acids, such as to alter a glycosylation site, a phosphorylation site or an acetylation site, or to minimize misfolding by substitution or deletion of one or more cysteine residues that are not necessary for function. Conservative amino acid substitutions are those that preserve the general charge, hydrophobicity/hydrophilicity, and/or steric bulk of the amino acid substituted. Variants can be designed so as to retain or have enhanced biological activity of a particular region of the protein (e.g., a functional domain and/or, where the polypeptide is a member of a protein family, a region associated with a consensus sequence). Selection of amino acid alterations for production of 3-KSR variants can be based upon the accessibility (interior vs. exterior) of the amino acid (see, e.g., Go et al., 15 INT. J. PEPTIDE PROTEIN RES. 211 (1980)), the thermostability of the variant polypeptide (see, e.g., Querol et al., 9 PROT. ENG. 265 (1996)), desired glycosylation sites (see, e.g., Olsen and Thomsen, 137 J. GEN. MICROBIOL. 579 (1991)), desired disulfide bridges (see, e.g., Clarke et al., 32 BIOCHEM. 4322 (1993); and Wakarchuk et al., 7 PROTEIN ENG. 1379 (1994)), desired metal binding sites (see, e.g., Toma et al., 30 BIOCHEM. 97 (1991), and Haezerbrouck et al., 6 PROTEIN ENG. 643 (1993)), and desired substitutions within proline loops (see, e.g., Masui et al., 60 APPL. ENV. MICROBIOL. 3579 (1994)). Cysteine-depleted muteins can be produced as disclosed in U.S. Pat. No. 4,959,314.

3-KSR variants also include fragments of the polypeptides disclosed herein, particularly biologically active fragments and/or fragments corresponding to functional domains. Fragments of interest will typically be at least about 10 amino acids (aa) to at least about 15 aa in length, usually at least about 50 aa in length, and can be as long as 300 aa in length or longer, but will usually not exceed about 531 aa in length, where the fragment will have a stretch of amino acids that is identical to a 3-KSR polypeptide encoded by a polynucleotide having a sequence of any one of the polynucleotide sequences provided herein, or a homolog thereof. The genetic code can be used to select the appropriate codons to construct the corresponding variants. In particular, fragments will include those that contain the specific domains or epitopes of the 3-KSR protein.

Amino acid sequence variants of 3-(SR may be prepared by introducing appropriate nucleotide changes into the nucleic acid, or by peptide synthesis. Such modifications include, for example, deletions from, and/or insertions into and/or substitutions of, residues within the amino acid sequences of 3-KSR. Any combination of deletion, insertion, and substitution is made to arrive at the formal 3-KSR construct, provided that the final construct possesses the desired characteristics. The amino acid changes also may alter post-translational processes of 3-KSR, such as changing the number or position of glycosylation sites or other post-translational modifications including acetylation and phosphorylation.

A useful method for the identification of certain residues or regions of 3-KSR that are preferred locations for mutagenesis is called "alanine scanning mutagenesis" as described by Cunningham and Wells, 244 SCIENCE 1081-85 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed 3-KSR variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include a 3-KSR with an N-terminal methionyl residue.

Another type of variant is an amino acid substitution variant. These variants have at least one amino acid residue in the 3-KSR protein replaced by a different residue.

Substantial modifications in the biological properties of the 3-KSR protein are accomplished by selecting substitutions that differ significantly in their effect on maintaining (i) the structure of the polypeptide backbone in the area of the substitution, for example, as a sheet or helical conformation, (ii) the charge or hydrophobicity of the molecule at the target site, or (iii) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class. Conservative substitutions involve exchanging of amino acids within the same class.

II. Vectors Encoding 3-KSR

The present invention further provides vectors for expressing any enzyme in the biochemical pathway for mammalian sterol biosynthesis, such as the enzyme, 3-KSR in cells auxotrophic for cholesterol. Generally, any prokaryotic cloning vector may be used for the construction of the vector. The vector may comprise a bacterial origin of replication, which is useful for the propagation of the vector in a host strain of *E. coli* from which the vector DNA will be isolated prior to transfection of mammalian cells. Examples of bacterial origins of replication include, but are not limited to, Col E1, pUC, pBR322, or others sourced from non-pathogenic strains of *E. coli*. The vector may further comprise a selection marker for high copy number expansion of the plasmid in E. coli. Exemplary selection markers include genes that confer resistance to antibiotics such as ampicillin, carbenicillin, tetracycline, chloramphenicol, kanamycin, gentamycin, sulphaethoazole, trimethoprim, and others. Additional selection markers that may be used in the vectors of the present invention include genes conferring selection based on heat shock, metal detoxification, and other metabolic processes.

The vector may further comprise a eukaryotic promoter to drive expression of the 3-KSR gene. This can be a minimal promoter, such as the mammalian thymidine kinase (TK) gene promoter, or a stronger transcription cassette, such as the Simian Virus 40 (SV40) origin of replication and early promoter region. Very strong promoters, such as the Cytomegalovirus (CMV) Major Immediate Early (MIE) promoter region, with or without the intron A and/or B sequences, or the human Elongation Factor-1 Alpha (EFα), may also be used to drive expression of the 3-KSR gene. A eukaryotic transcriptional termination sequence, or poly-adenylation site may also be present to stop transcription and signal poly-adenylation of the 3-KSR gene. The poly-adenylation site may theoretically be derived from any eukaryotic gene, but commonly used strong poly-adenylation sequences include the SV40 late poly-A and the Bovine Growth Hormone (BGH) poly-A.

Figure 2:
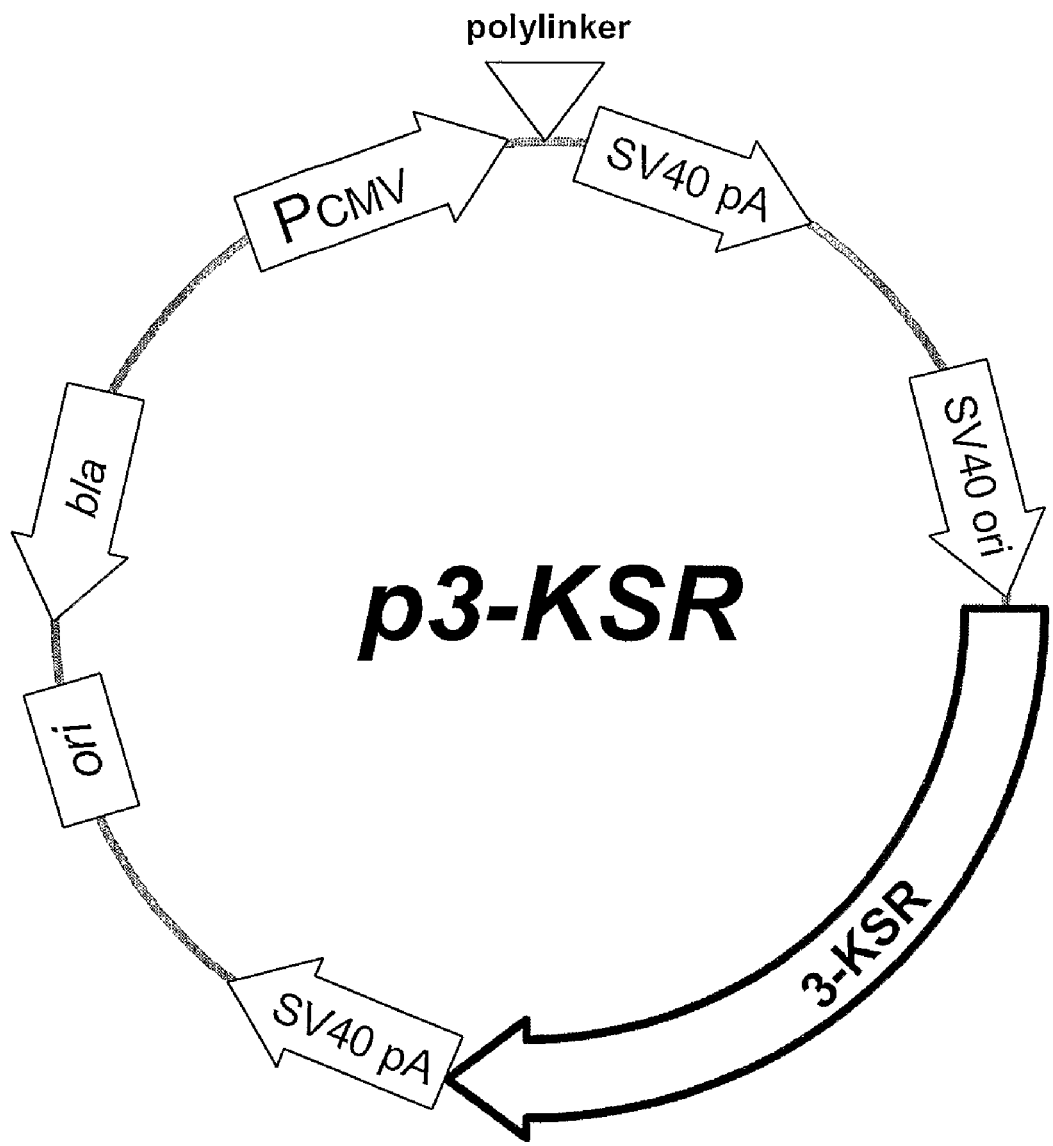
FIG. 2 depicts the plasmid map of p3-KSR expression vector.

As depicted in FIG. 2, one embodiment of a vector (in this case, named p3-KSR), may comprise a pUC-derived bacterial origin of replication (ori) and a beta-lactamase gene (bla) that confers ampicillin or carbenicillin resistance in E. coli strains sensitive to these antibiotics. The vector may also contain the Cytomegalovirus (CMV) Major Immediate Early (MIE) promoter and enhancer to drive expression of heterologous recombinant sequences cloned into the polylinker region. The Simian Virus 40 (SV40) poly adenylation sequence (SV40 pA) can be located downstream of both the heterologous recombinant sequences and the 3-KSR gene to efficiently polyadenylate the nascent mRNAs from each gene. The SV40 promoter and origin of replication (SV40 ori) may be located immediately upstream of the 3-KSR gene to drive expression of this selection marker.

In a specific embodiment, the 3-KSR gene may be inserted into a vector by direct cloning of the murine 3-KSR cDNA amplified from a mouse kidney cDNA library. Primers engineered to amplify 3-KSR from a mouse kidney cDNA library may contain, for example, Pm1I ends, which are compatible with a Pm1I site present in the pUC-derived vector, p3-KSR, and which site is present in the region between the SV40 ori and the SV40 poly-A. Thus, a 3-KSR cDNA restricted with Pm1I may be used to clone this gene into the Pm1I site of the p3-KSR backbone. The orientation of the gene in the vector may be determined by restriction endonuclease analysis (REN), and dideoxy-termination DNA sequencing.

Figure 3:
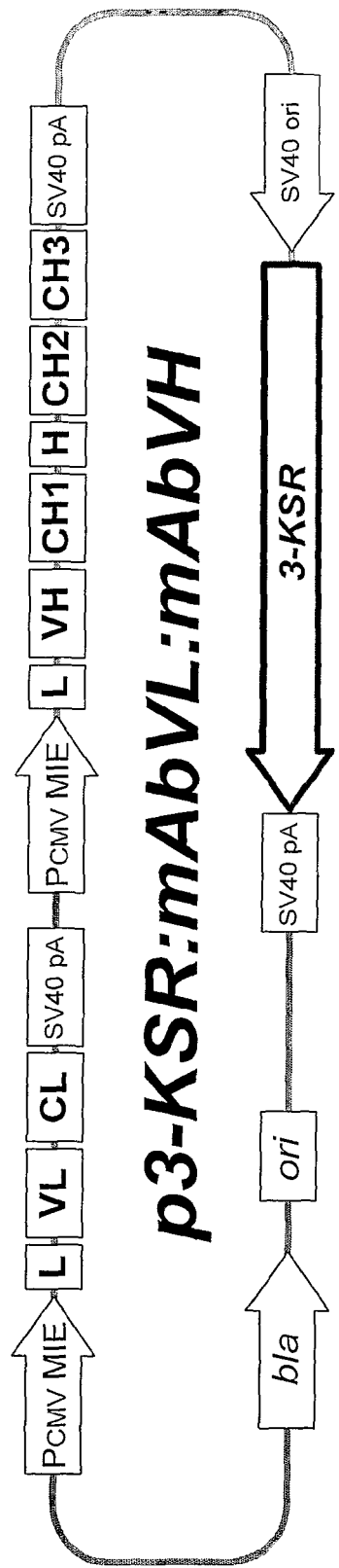
FIG. 3 depicts the plasmid map of p3-KSR:mAbVL: mAbVH expression vector carrying complete human antibody light and heavy chain genes cloned in tandem.
Figure 4:
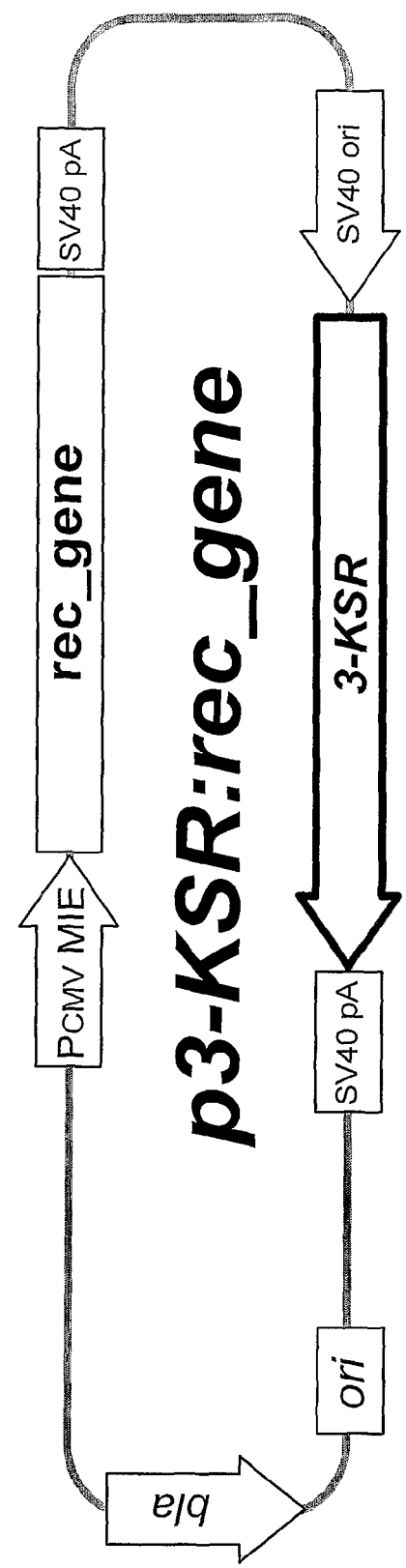
FIG. 4 depicts the plasmid map of p3-KRS:rec_gene, an example of a recombinant gene construct (rec_gene) cloned into p3-KSR.
Figure 5:
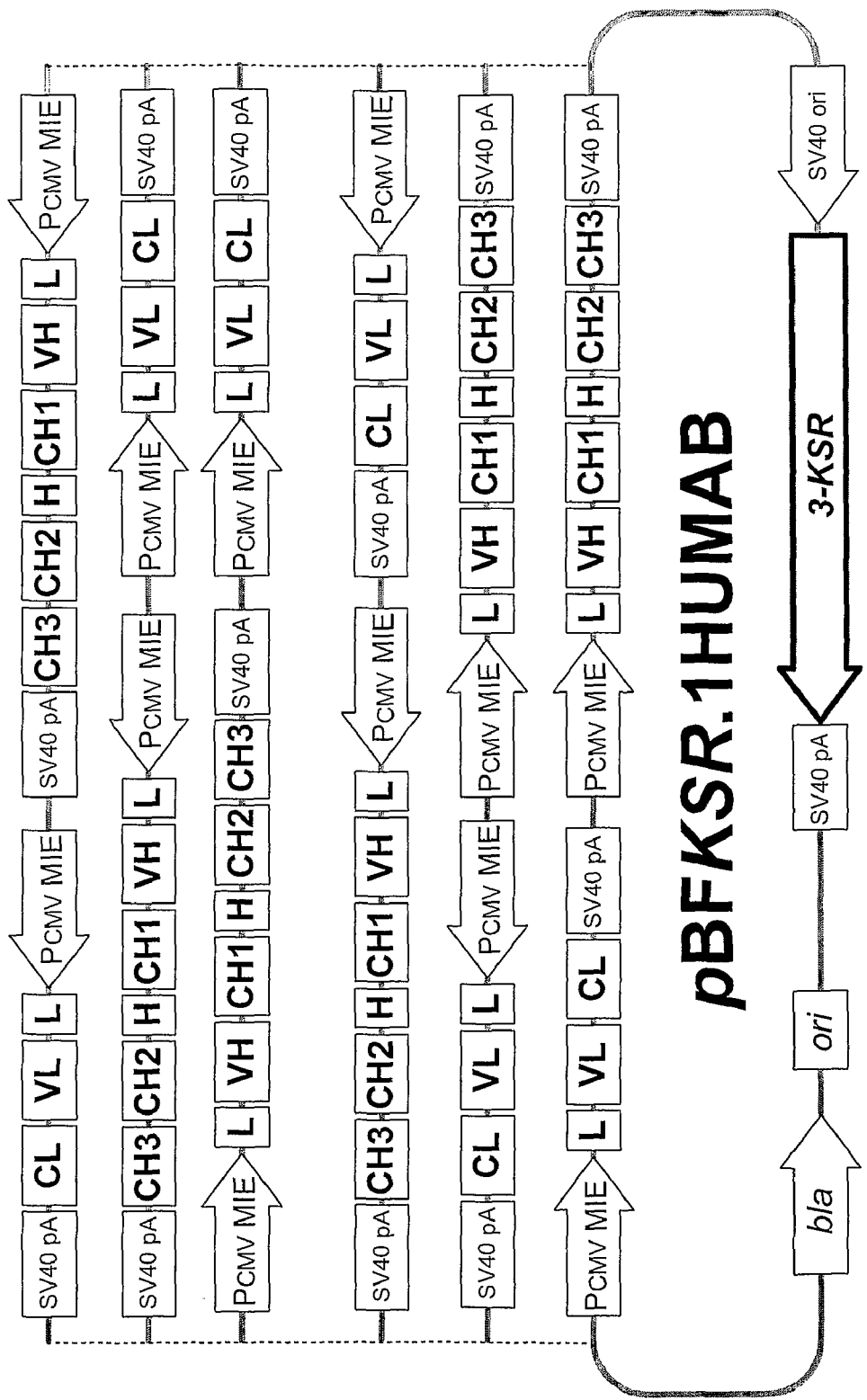
FIG. 5 depicts pBFKSR.1HUMAB which provides an example of 6 possible antibody gene cassette expression orientations in the multiple cloning region of the p3-KSR expression vector.

A polynucleotide or gene or a cassette encoding at least one heterologous polypeptide of interest is then inserted into the vector comprising the 3-KSR gene at a multiple cloning region or site as shown for example in FIG. 3, 4, or 5. The inserted polynucleotides or cassettes are under the control of or operably linked to a promoter that will allow expression in a eukaryotic or preferably a mammalian host cell.

III. Transfection of Cells with Vectors Encoding 3-KSR

The introduction of polynucleotide vectors encoding heterologous proteins of interest (and 3-KSR as a selection marker) into host cells may be accomplished using techniques well known in the art including, but not limited to, electroporation, lipofection, calcium phosphate precipitation, polyethylene glycol precipitation, sonication, transfection, transduction, transformation, and viral infection. See SAMBROOK ET AL., MOLECULAR CLONING: A LABORATORY MANUAL (3d ed. 2001).

Any eukaryotic cell, preferably mammalian, whose cholesterol auxotrophy is attributable to enzyme activity, such as 3-KSR activity, may be used for transfection. Exemplary cell lines may include, but are not limited to, NS-0 (ECACC No. 85110503), NS-1 (ECACC No. 85011427), and CHO-215 (Plemenitas et al., 265(28) J. Biol. Chem. 17012-17 (1990)).

The present invention also encompasses eukaryotic cells, and specifically mammalian cells, that are not initially auxotrophic for cholesterol but are made so by using radiation, mutagenic agents or recombinational gene knockout techniques to inactivate endogenous genes encoding for 3-KSR activities including, but not limited to, 17β-hydroxysteroid dehydrogenase type 7 (Hsd17b 7) and 3β-hydroxy-delta(5)-steroid dehydrogenase (Hsd3b5). In yet another embodiment, the targeted knockout gene may include, but is not limited to, rat 3β-Hsd III, mouse 3β-Hsd IV, mouse 3β-Hsd V and hamster 3β-Hsd III, which are known to function exclusively as 3-ketosteroid reductases.

NS-0, NS-1, CHO-215, and other cholesterol-auxotrophic cell lines that are transfected with an expression vector which contains the 3-KSR selection marker (and a polynucleotide encoding a heterologous protein of interest) should be grown in medium lacking cholesterol. In certain other embodiments, the host cells may be grown in any serum-free and cholesterol-free medium which contains the following non-exhaustive list of sterol precursors: 4-methyl-5α-cholesta-3,8,24-triene-3'-ol, 3-oxo-4α-methyl-5α-cholesta-8,24-diene, 5α-cholesta-3,8,24-triene-3β-ol, and/or 3-oxo-5α-cholesta-8,24-diene. These precursors act upstream of 3-KSR in the biochemical pathway of cholesterol.

To address regulatory concerns, the host cells (before or after transfection) may be grown in any suitable media including, but not limited to, serum-free media, protein-free media, chemically defined media, or any combination thereof including chemically defined/serum-free media. This particular aspect of the present invention addresses concerns that animal-derived proteins and/or proteins of unknown origin may render recombinant protein products unsuitable for human therapeutic or diagnostic use. One specific embodiment of a suitable growth medium is CD Hybridoma Medium (Invitrogen® Corp., Carlsbad, Calif.), a chemically defined, serum-free medium that contains no proteins of animal, plant, or synthetic origin and has been confirmed to be free of undefined lysates or hydrolysates.

The host cells of the present invention may be provided as already adapted to an appropriate growth medium, such as CD-SFM. Often, cells are adapted to such media prior to transfection. In that case, cells may be adapted to HyQ® CDM4NS-0 (Hyclone®, Logan, Utah), which is another chemically defined, serum-free medium that is devoid of animal-derived components. The latter commercially available medium includes sufficient amounts of cholesterol to support the growth of cholesterol auxotrophic cell lines. After transfection, the cells are grown in a suitable selection medium without cholesterol. Alternatively, the transfectants are cultured in cholesterol-free medium using classical media supplemented with serum that has been extensively delipidated using known techniques and found to not support growth of parental cells.

Following transfection, the cells are typically seeded at low densities to select for stable transformants. In this regard, any appropriate selection medium may be used. In one embodiment, the selection medium may comprise CD Hybridoma supplemented with 2 mM L-Glutamine or Glutamax and 1×NEAA (non-essential amino acids) (Invitrogen® Corp., Carlsbad, Calif.).

In certain embodiments, a cocktail of growth supplements may be added to the selection medium to optimize growth conditions after transfection. The growth supplements may be added post-transfection to any appropriate cell line including, but not limited to, NS-0, NS-1, CHO-215 cells. In a specific embodiment, the cocktail of growth supplements may be used to optimize post-transfection growth conditions for NS-0 cells. In one embodiment, the growth supplements may comprise, but are not limited to, serum albumin, interleukin-6, insulin, sodium selenite, sodium pyruvate, and ethanolamine.

Any appropriate, commercially available version of serum albumin may be used including, but not limited to, bovine serum albumin (BSA), bovine serum albumin fraction v, and whole human serum albumin. In certain embodiments, the serum albumin may be fatty-acid free, instead of unmodified, in order to remove possible cholesterol-serum albumin complexes that may supply the lipid to growing cells. Fatty-acid free BSA is available from numerous companies including, for example, Research Organics, Inc., Cleveland, Ohio. Final concentration of this component may include, but is not limited to, a range from about 0.1% to about 5% in selection medium, more specifically, about 0.2%, about 0.5%, about 1.0%, about 1.5%, about 2.0% or more up to about 5.0%. In a specific embodiment, final concentration of serum albumin may be about 1% in selection medium.

Another growth supplement that may be used to optimize growth conditions includes interleukin-6. In one embodiment, recombinant human IL-6 may be used (Promega Corp., Madison, Wis.). Final concentration of IL-6 may include, but is not limited to, a range from about 1 ng/mL to about 9 ng/mL in selection medium, more specifically, about 2 ng/mL, about 3 ng/mL, about 4 ng/mL, about 5 ng/mL, about 6 ng/mL or more, up to about 9 ng/mL. In a specific embodiment, the final concentration of IL-6 may be about 5 ng/mL in selection medium. Concentrations of IL-6, such as rhIL-6, may be adjusted from batch to batch, as necessary, to target the manufacturer's reported EC50 for the cytokine.

The cocktail of growth supplements may further include insulin, specifically, recombinant human insulin (RayBiotech, Inc., Norcross, Ga.). Final concentration of this component may include, but is not limited to, a range from about 5 mg/L to about 15 mg/L in selection medium, more specifically, about 6 mg/L, about 7 mg/L, about 8 mg/L, about 9 mg/L, about 10 mg/L, about 11 mg/L or more, up to about 15 mg/L. In a specific embodiment, the final concentration of insulin may be about 10 mg/L in selection medium.

Sodium selenite may also be used to optimize growth conditions (J. T. Baker, Phillipsburg, N.J.). Final concentration of this supplement may include, but is not limited to, a range from about 5.0 μg/L to about 8.0 μg/L in selection medium, more specifically about 5.5 μg/L, about 6.0 μg/L, about 6.5 μg/L, about 7.0 μg/L or more, up to about 8.0 μg/L. In a specific embodiment, the final concentration of sodium selenite may be about 6.7 μg/L in selection medium.

In other embodiments, sodium pyruvate may be used a growth supplement (SAFC Biosciences, Inc., Lenexa, Kans.). Final concentration of sodium pyruvate may include, but is not limited to, a range from about 0.01 g/L to about 0.3 g/L in selection medium, more specifically, about 0.05 g/L, about 0.1 g/L, about 0.15 g/L or more, up to about 0.3 g/L. In a specific embodiment, the final concentration of sodium pyruvate may be about 0.11 g/L in selection medium.

The cocktail of growths supplements may further include ethanolamine (Sigma-Aldrich® Co., St. Louis, Mo.). Final concentration of this supplement may include, but is not limited to, a range from about 0.5 mg/L to about 3.5 mg/L, more specifically, about 1.0 mg/L, about 1.5 mg/L, about 2.0 mg/L, about 2.5 mg/L or more, up to about 3.5 mg/L. In a specific embodiment, the final concentration of ethanolamine may be about 2.0 mg/L in selection medium.

In a specific embodiment, the cocktail of growth supplements may comprise fatty acid-free BSA (0.1%-5%), rhIL-6 (1 ng/mL-9 ng/mL), recombinant human insulin (5 mg/L-15 mg/L), sodium selenite (5 μg/L-8 μg/L), sodium pyruvate (0.01 g/L-0.3 g/L), and ethanolamine (0.5 mg/L-3.5 mg/L) (final concentrations in selection medium). In another specific embodiment, the cocktail of growth supplements may comprise fatty acid-free BSA (1%-5%), rhIL-6 (0.5 μg/mL), recombinant human insulin (10 mg/L), sodium selenite (6.7 μg/L), sodium pyruvate (0.11 g/L), and ethanolamine (2 mg/L) (final concentrations in selection medium). In yet another embodiment, the cocktail of growth supplements may comprise fatty acid-free BSA (1%), rhIL-6 (0.5 ng/mL), recombinant human insulin (10 mg/L), sodium selenite (6.7 μg/L), sodium pyruvate (0.11 g/L), and ethanolamine (2 mg/L) (final concentrations in selection medium).

In another embodiment, the growth supplements may comprise fatty acid-free BSA, rhIL-6, recombinant human insulin, sodium selenite, sodium pyruvate, ethanolamine, and no other growth supplements. In a further embodiment, the growth supplements may comprise fatty acid-free BSA, rhIL-6, recombinant human insulin, sodium selenite, sodium pyruvate, ethanolamine, and no other substance typically involved or used in the growth of cultured cells. In an alternative embodiment, the growth supplements may comprise fatty acid-free BSA, rhIL-6, recombinant human insulin, sodium selenite, sodium pyruvate, ethanolamine, and no other substance typically found in serum. In yet another embodiment, the growth supplements may comprise fatty acid-free BSA, rhIL-6, recombinant human insulin, sodium selenite, sodium pyruvate, ethanolamine, any substance typically used to reconstitute any of the recited growth supplements including water, and no other substance whatsoever.

IV. Kits for Producing Heterologous Proteins

The present invention further provides kits for commercial sale. In certain embodiments, the kit may comprise a vector, a plurality of cells, and growth supplements. The vector may comprise a sequence encoding an enzyme in the biochemical pathway for mammalin sterol biosynthesis, such as for example, 3-KSR, useful for the selection of cells transfected with the vector. Users of the kit may clone a target gene into the vector using an appropriate restriction enzyme(s). In certain embodiments, the cells are auxotrophic for cholesterol. In one embodiment, the cells provided in the kit may already be adapted to grow in chemically defined media. In another embodiment, the cells provided in the kit may already be adapted to grow in chemically defined, serum-free media. In response to regulatory requirements, the cells may be derived from a working cell bank which would be determined to be free of adventitious agents.

In another embodiment, the kit may comprise growth supplements, as described herein, that support growth of cells including, but not limited to, NS-0, NS-1, and CHO-215 and cells. In certain embodiments, the kit may comprise growth supplements that support the growth of cells in serum-free media, protein-free media, chemically defined media, or any combination thereof including chemically defined/serum-free media. In a specific embodiment, the kit may comprise growth supplements, as described herein, that support the growth of CD-SFM NS-0 cells at low seeding densities, for example, during the post-transfection and limiting dilution cell cloning (LDCC) phase.

Furthermore, the kits of the present invention may be used to express any heterologous protein of interest. Indeed, the nature and source of the heterologous protein expressed in the cells, cell lines, and cell cultures of the present invention are not limited. For example, plasmid p3-KSR may be engineered for expression of a single or at least two genes. The former is applicable for expression of standalone proteins, such as a single chain hormone, and the latter is meant for expression of a dual chain molecule, such as an antibody.

In a specific embodiment of the present invention, a recombinant antibody molecule may be expressed using the vector containing the necessary genes. See for example, FIG. 3. Antibodies are complex proteins made up of multiple components, specifically two heavy chains and two light chains. In one embodiment, the p3-KSR vector may be engineered to include complete heavy and light chain genes for human Immunoglobulin G (IgG) cloned in tandem. Protein expression from this recombinant construct results in the secretion of a monoclonal antibody that can subsequently be isolated from the cell culture and purified for commercial use. Human monoclonal antibodies are well-suited to be applied as human therapeutics because they are specific to a single antigen and can be used to target specific pathogens, organs, or tumors.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

Example 1

Demonstration of Cholesterol Selection of the Murine Myeloma Cell Line NS-0 in Chemically Defined Serum-Free Medium The murine myeloma cell line NS-0 was adapted to two independent chemically defined serum-free medium (CD-SFM) formulations to test the suitability of 3-KSR as a selection marker in this cell background, and in SFM conditions from the onset. NS-0 cells were adapted to CD-Hybridoma (Invitrogen®) and CDM-4-NS-0 (HyClone®). Accession cell banks (ACB) were generated for each of the CD-SFM-adapted NS-0 cell lines. An assay was setup to determine the dependence of CD-SFM-NS-0 cell lines on cholesterol supplementation in the growth medium. These assays showed that 72 hours after culturing CD-SFM-NS-0 cells in medium without cholesterol, fewer than 10% of the cells remain alive. In as few as 5 days following culturing in CD-SFM, no live cells could be detected by Trypan Blue exclusion analysis. In addition, an intermittent growth phase of these cells in the absence of cholesterol was not observed, revealing the sensitivity to the lack of this lipid in the culture medium.

Example 2

PCR Amplification of a Murine 3-Ketosteroid Reductase (3-KSR) and Cloning of a 3-KSR into an Expression Vector A murine 3-ketosteroid reductase (3-KSR) gene coding for Mus musculus 3β-hydroxy-delta(5)-steroid dehydrogenase (Hsd3b5) was amplified from cDNAs generated from adult male BALB/c kidneys. After PCR amplification using oligonucleotides specific for the published sequence of the murine 3-KSR Hsd3b5, a distinct band of about 1.1 kb was detected by agarose gel electrophoresis. This band was isolated and cloned into pCR-Blunt II-TOPO vector (Invitrogen®), and subsequently recloned into the pBFdhfr.1 background, in lieu of dhfr. The new construct is called pBFksr.1.

The 1.1 kb coding region of 3-ksr in pBFksr.1 was confirmed by DNA sequencing, and its open reading frame (orf) was compared to the published sequence. The determined sequence matched 100% with the published murine 3-ketosteroid reductase with NCBI accession number A49573.

Example 3

Transfection and Selection of NS-0 Cells in Chemically-Defined Fatty Acid-Free Supplemented Selection Medium A construct pBFksr.1 containing a correct 3-KSR orf is transfected into NS-0 cells and selected in chemically-defined fatty acid-free supplemented selection medium. The medium consists of the following: CD-Hybridoma (Invitrogen®), Glutamax (2 mM, Invitrogen®), NEAA (non-essential amino acids) (1×, Invitrogen®), Fatty-acid free BSA (1%, Calbiochem), Recombinant human IL-6 (5 ng/ml, Promega), ITS Liquid Media Supplement (1×, Sigma-Aldrich). The initial transfection and selection is performed "in bulk," in T-75 flasks as follows. On the day of transfection, the NS-0 parental culture is counted using the Trypan blue exclusion method to differentiate between live and dead cells. The culture should be at least 90% viable. For each transfection, about $1 \times 10^7$ cells are required. In addition to the plasmid transfections, one "mock" transfection (without DNA) should be performed to establish a negative control. The cells are centrifuged and washed by resuspending the cell pellet in 20 mL of serum-free transfection medium and centrifuging once more. For each transfection, $1 \times 10^7$ cells are resuspended in 700 μL of serum-free transfection medium. The DNA solution is prepared by resuspending 40 μg of the purified linearized plasmid DNA in 100 μL of distilled sterile water. Linearization of DNA is achieved with any DNA restriction endonuclease, commonly but not restricted to PvuI (*Proteus vulgaris* restriction endonuclease I), which restricts pBFksr.1 once, in the beta-lactamase open reading frame (orf). This entire DNA solution is added to an electroporation cuvette. The 700 μL of cell suspension is added to the DNA solution in the cuvette and mixed gently by pipetting, avoiding the creation of bubbles. The cap is placed on the cuvette and the cuvette is placed in the electroporation apparatus (Gene Pulser II (Bio-Rad Laboratories, Inc., Hercules, Calif.) or equivalent). A single pulse of 250 volts, 400 μFd is delivered to the cuvette (field strength of 625 V/cm). Optimum conditions should give a time constant value no greater than 8 milliseconds. The cells are added to 12 mL of chemically-defined fatty acid-free supplemented selection medium in a T-75 cell culture flask and allowed to incubate at 37° C., 5% $CO_2$, 90% relative humidity overnight.

The culture transfected with pBFksr.1 and selected in chemically-defined fatty acid-free supplemented selection medium produce statistically significant numbers of live cells after a 3-week selection relative to controls. Mock transfected NS-0 cells grown in the same selective conditions do not produce statistically significant numbers of live cells after a 3-week selection.

Example 4

Transfection, Selection, and Expression of a Monoclonal Antibody in NS-0 Cells in Chemically-Defined Fatty Acid-Free Supplemented Selection Medium The mammalian expression vector pBFdhfr.1 was constructed and serves as the backbone for the cloning of mammalian genes, including human antibody heavy and light chain coding sequences, for expression in the dihydrofolate reductase (dhfr) mutant parental cell line CHO-DG44. Using this vector, a human IgG1 heavy chain constant region expression cassette was cloned in the multiple cloning site (mcs), and serves as acceptor for human heavy chain variable sequences. This vector was designated pBFdhfr.1:Hcassette.

The corresponding light chain variable sequences were first cloned into a baculovirus expression vector containing a human light chain constant region cassette, pIEI-light. The entire light chain coding sequence was subsequently cloned into pBFdhfr.1. To construct a dual expression vector, primers specific to the 5' end of pCMV-MIE and to the BGH-pA on the complementary strand were used to amplify a light chain cassette containing pCMV-MIE-light chain-BGHpA, which contained BglII REN sites on both ends. This fragment was subsequently cloned into the unique BglII site in each corresponding pdhfr:Heavy_Chain construct. The resulting construct, pBFdhfr.1:humAb contains complete human antibody light and heavy chain genes cloned in tandem.

The murine 3-ketosteroid reductase (3-KSR) gene is isolated and cloned into pCR-Blunt 1'-TOPO vector (Invitrogen®), and subsequently recloned into the pBFdhfr.1:humAb construct, in lieu of dhfr. This new construct, pBFksr.1:HUMAB containing a correct 3-KSR orf is transfected into NS-0 cells and selected in chemically-defined fatty acid-free supplemented selection medium. The initial transfection and selection is performed "in bulk," in T-75 flasks. Following transfection, cells are cultured directly in selection medium.

The culture transfected with pBFksr.1:HUMAB and immediately selected in cholesterol free medium produce statistically significant numbers of live cells after a 3-week selection relative to controls. Mock transfected NS-0 cells grown in the same selective conditions do not produce statistically significant numbers of live cells after a 3-week selection.

Upon selection and growth of transfected cells, cell free supernatants are assayed for recombinant mAb by enzyme linked immunosorbant assay (ELISA). Briefly, supernatants of cultures transfected with pBFksr.1:HUMAB are sampled and centrifuged to remove any cells and debris. Ninety six-well plates are coated with a goat anti-human Fab lambda specific antibody (Sigma-Aldrich® Co., St. Louis, Mo.) solution formulated by adding 9 µL to 6.3 mL of phosphate buffered saline (PBS). Plates are incubated for at least 24 hours and no more than 2 weeks at 4° C. On day of assay, plates are rinsed 3 times with PBS/tween buffer (0.1% tween in PBS). A human IgG1 lambda monoclonal antibody standard (Sigma®) is diluted to 5 µg/mL in PBS/tween and serially diluted in PBS/tween at a 1:2 ratio to generate a standard concentration panel. Each standard is added to the 96-well plate at 100 µL per well. Samples of u known antibody concentration are diluted 1:2000 in PBS/tween and added to the 96-well plate at 100 µL per well. The plate is incubated for 1 hour at room temperature. After incubation, the plate is washed 3 times with PBS/tween. A peroxidase-labelled goat anti-human IgG Fc antibody (KPL, Inc., Gaithersburg, Md.) is diluted 1:2000 in PBS/tween and added to the 96-well plate at 100 µL per well. The plate is incubated for 1 hour at room temperature. After incubation, the plate is washed 3 times with PBS/tween. A 3,3',5,5' tetramethylbenzidine (TMB) substrate (Sigma®) is added to the 96-well plate at 100 µL per well. The reaction is stopped after approximately 1 minute with the addition of 100 µL of 0.5 M $H_2SO_4$ (Acros Organics, Geel, Belgium). The plate is read at a wavelength of 450 nm in a ThermoMax microplate reader or equivalent. ELISA results show positive for the presence of the recombinant mAb product.

What is claimed is:

1. A host cell transformed with a vector comprising a polynucleotide encoding a 3-ketosteroid reductase and a polynucleotide encoding a heterologous polypeptide, wherein the host cell is a eukaryotic cell and is auxotrophic for cholesterol.

2. The host cell of claim 1, wherein said 3-ketosteroid reductase comprises a murine 3-ketosteroid reductase.

3. The host cell of claim 1, wherein said polynucleotide encoding said reductase comprises SEQ ID NO: 1 or SEQ ID NO:2, or encodes an amino acid sequence comprising SEQ ID NO:3 or SEQ ID NO:4.

4. The host cell of claim 1, wherein said vector is a recombinant DNA expression vector.

5. The host cell of claim 4, wherein the recombinant DNA expression vector further comprises at least a first transcription unit under control of the human cytomegalovirus promoter.

6. The host cell of claim 1, wherein said host cell is selected from the group consisting of NS-O, NS-I, and CHO-215.

7. The host cell of claim 1, wherein said host cell is an NS-O mouse myeloma cell.

8. A kit comprising:
 a vector comprising a polynucleotide that encodes a 3-ketosteroid reductase;
 a plurality of host cells that are auxotrophic for cholesterol;
 chemically defined, serum-free media;
 growth supplements that support the growth of said plurality of host cells at low-seeding and clonal densities; and
 at least one protocol to utilize said kit.

9. The kit of claim 8, wherein said 3-ketosteroid reductase comprises a murine 3-ketosteroid reductase.

10. The kit of claim 8, wherein said polynucleotide encoding said reductase comprises SEQ ID NO:1 or SEQ ID NO:2, or encodes an amino acid sequence comprising SEQ ID NO:3 or SEQ ID NO:4.

11. The kit of claim 8, wherein said vector is a recombinant DNA expression vector.

12. The kit of claim 11, wherein the recombinant DNA expression vector further comprises at least a first transcription unit for a product gene under control of the human cytomegalovirus promoter.

13. The kit of claim 8, wherein said host cell is selected from the group consisting of NS-O, NS-I, and CHO-215.

14. The kit of claim 8, wherein said host cell is an NS-O mouse myeloma cell.

15. The kit of claim 8, wherein said host cells are adapted to chemically defined, serum-free medium.

16. The kit of claim 8, wherein said host cells are adapted to chemically defined medium.

17. The kit of claim 8, wherein said growth supplements comprise at least one of fatty acid-free BSA, rhIL-6, recombinant human insulin, sodium selenite, sodium pyruvate, and ethanolamine.

18. The kit of claim 8, wherein said growth supplements comprise final concentrations in the chemically defined, serum free media of 0.1% to 5% fatty acid-free BSA, 1 ng/mL to 9 ng/mL rhIL-6, 5 mg/mL to 15 mg/L recombinant human insulin, 5 μg/L to about 8 μg/L sodium selenite, 0.01 g/L to 0.3 g/L sodium pyruvate, and 0.5 mg/L to 3.5 mg/L ethanolamine.

19. The kit of claim 8, wherein said growth supplements comprise final concentrations in the chemically defined, serum free media of 1% fatty acid-free BSA, 5 ng/mL rhIL-6, 10 mg/L recombinant human insulin, 6.7 μg/L sodium selenite, 0.11 g/L sodium pyruvate, and 2.0 mg/L ethanolamine.

20. A composition of cell culture supplements comprising 0.1% to 5% fatty acid-free BSA, 1 ng/mL to 9 ng/mL rhIL-6, 5 mg/mL to 15 mg/L recombinant human insulin, 5 μg/L to 8 μg/L sodium selenite, 0.01 g/L to 0.3 g/L sodium pyruvate, and 0.5 mg/L to 3.5 mg/L ethanolamine.

21. The composition of claim 20 comprising 1% fatty acid-free BSA, 5 ng/mL rhIL-6, 10 mg/L recombinant human insulin, 6.7 μg/L sodium selenite, 0.11 g/L sodium pyruvate, and 2.0 mg/L mg/L ethanolamine.

22. A method of making a cell that is auxotrophic for cholesterol able to survive in cholesterol-free medium, the method comprising:
    transfecting a eukaryotic cell that is auxotrophic for cholesterol with a vector comprising a polynucleotide that encodes a 3-ketosteroid reductase and optionally at least one polynucleotide that encodes a heterologous protein; and
    wherein said polynucleotide that encodes the 3-ketosteroid is expressed by the transfected cell to confer the ability to survive in cholesterol-free medium.

23. The method of claim 22, wherein said cells are selected from the group consisting of NS-0, NS-1, and CHO-215.

24. The method of claim 23, wherein said cells are NS-O mouse myeloma cells.

25. The method of claim 22, wherein said medium is chemically defined and serum-free or chemically defined.

26. A method for obtaining cells that have the ability to survive in a medium lacking cholesterol and have the ability to express a heterologous protein comprising:
    transfecting eukaryotic cells that are auxotrophic for cholesterol with a vector comprising a polynucleotide encoding a 3-ketosteroid reductase, and at least one polynucleotide that encodes a heterologous protein; and
    selecting the cells that have the ability to survive in medium lacking cholesterol.

27. The method of claim 26, wherein said cells are selected from the group consisting of NS-O, NS-I, and CHO-215.

28. The method of claim 27, wherein said cells are NS-O mouse myeloma cells.

29. The method of claim 26, wherein said medium is chemically defined and serum-free or chemically defined.

30. A method of expressing a heterologous protein comprising transfecting a cell that is auxotrophic for cholesterol with a vector comprising a polynucleotide encoding a 3-ketosteroid reductase, wherein the vector further comprises a polynucleotide encoding the heterologous protein; and culturing the transfected cell in a cholesterol-free medium under conditions to provide expression of said heterologous protein.

31. The method of claim 30, wherein said cells are selected from the group consisting of NS-O, NS-I, and CHO-215.

32. The method of claim 31, wherein said cells are NS-O mouse myeloma cells.

33. The method of claim 30, wherein said medium is chemically defined and serum-free or chemically defined.

* * * * *

```
SEQUENCE LISTING

<160> NUMBER OF SEQ ID NOS: 4

<210> SEQ ID NO 1
<211> LENGTH: 1122
<212> TYPE: DNA
<213> ORGANISM: Mus musculus

<400> SEQUENCE: 1
atgcctggat ggagctgcct ggtgacagga gcaggagggt ttcttggcca gaggattgtc      60
cgaatgttgg tgcaggagga agagttgcag gagatcagag ccctgttcag gaccttcggt     120
cgaaaacatg aagaggaatt gtccaagctg cagacaaagg ccaaggtgag agtactgaag     180
ggagacattc tggatgccca atgcctgaag agagcctgcc agggcatgtc tgctgtcatc     240
cacaccgctg ctgctattga ccccgtggt gccgcttcca gacagaccat cctagatgtc      300
aatctgaaag gtactcagct cctactggat gcttgtgtgg aagccagtgt gccaacattc     360
atctacagca gctcagtgct tgtggctgga ccaaattcct acaaggagat catcctgaat     420
gcccatgagg aagagcatca tgaaagcaca tggcctaacc catacccata cagcaaaagg     480
atggctgaga aggcagtgct ggcaacaaat gggagactcc tgaaaaatgg tggcactttg     540
catacttgtg ccttaagact cccttttcatc tatggggaag aatgccaagt cacttcaacc     600
```

```
actgtgaaaa cagcactgaa gaacaacagc ataattaaga aaaatgccac attctccatc     660
gccaacccag tgtatgtggg caatgcagcc tgggctcaca ttctggctgc aggagcctca     720
caggacccca agaagtcccc aagcatccaa ggacagttct attacatctc tgataacacc     780
cctcaccaaa gctatgatga tttaaattac accctgagca aggagtgggg cctctgcctt     840
gattctggct ggaggcttcc tctgtccctg ctttactggc ttgccttcct gctggaaact     900
gtgagcttcc tgctacgtcc agtttacaac tataggccac cctttacccg cctcttgatc     960
acagtgctaa atagcgtgtt taccatttcc tataagaaag ctcagcgcga tctaggctat    1020
cagccacttg tcagctggga ggaagccaag caaaaaacct cagagtggat tggaacacta    1080
gtgaagcagc acagggagac actacacaaa aagtcacagt ga                      1122
```

<210> SEQ ID NO 2
<211> LENGTH: 1005
<212> TYPE: DNA
<213> ORGANISM: Mus musculus

<400> SEQUENCE: 2

```
atgcggaagg tggttttgat caccggggcg agcagtggca ttgggctagc cctttgcggt      60
cgactgctgg cagaagacga tgacctccac ctgtgtttgg cgtgtaggaa cctgagcaaa     120
gcaagagctg ttcgagatac cctgctggcc tctcaccccct ccgccgaagt cagcatcgtg    180
cagatggatg tcagcagcct gcagtcggtg gtccggggtg cagaggaagt caagcaaaag    240
tttcaaagat tagactactt atatctgaat gctggaatcc tgcctaatcc acaattcaac    300
ctcaaggcat tttctgcgg catcttttca agaaatgtga ttcatatgtt caccacagcg    360
gaaggaattt tgacccagaa tgactcggtc actgccgacg ggttgcagga ggtgtttgaa    420
accaatctct ttggccactt tattctgatt cgggaactgg aaccacttct ctgccatgcg    480
gacaacccct ctcagctcat ctggacgtcc tctcgcaatg caaagaaggc taacttcagc    540
ctggaggaca tccagcactc caaaggcccg gaaccctaca gctcttccaa atatgctacc    600
gacctcctga atgtggcttt gaacaggaat ttcaaccaga agggtctgta ttccagtgtg    660
atgtgcccag gcgtcgtgat gaccaatatg acgtatggaa ttttgcctcc ctttatctgg    720
acgttgctcc tacccataat gtggctcctt cgcttttttg taaatgcgct cactgtgaca    780
ccgtacaacg gagcagaggc cctggtgtgg ctcttccacc aaaaaccgga gtctcttaat    840
cctctgacca atacgcgag cgccacctcg ggatttggga ctaattacgt cacgggccaa    900
aagatggaca tagatgaaga cactgctgaa aaattctatg aggtcttact ggagctggaa    960
aagcgtgtca ggaccaccgt tcagaaatcg gatcacccga gctga                   1005
```

<210> SEQ ID NO 3
<211> LENGTH: 373
<212> TYPE: PRT
<213> ORGANISM: Mus musculus

<400> SEQUENCE: 3

```
Met Pro Gly Trp Ser Cys Leu Val Thr Gly Ala Gly Gly Phe Leu Gly
1               5                   10                  15

Gln Arg Ile Val Arg Met Leu Val Gln Glu Glu Glu Leu Gln Glu Ile
            20                  25                  30

Arg Ala Leu Phe Arg Thr Phe Gly Arg Lys His Glu Glu Leu Ser
        35                  40                  45

Lys Leu Gln Thr Lys Ala Lys Val Arg Val Leu Lys Gly Asp Ile Leu
    50                  55                  60
```

```
Asp Ala Gln Cys Leu Lys Arg Ala Cys Gln Gly Met Ser Ala Val Ile
 65                  70                  75                  80

His Thr Ala Ala Ala Ile Asp Pro Arg Gly Ala Ala Ser Arg Gln Thr
                 85                  90                  95

Ile Leu Asp Val Asn Leu Lys Gly Thr Gln Leu Leu Leu Asp Ala Cys
            100                 105                 110

Val Glu Ala Ser Val Pro Thr Phe Ile Tyr Ser Ser Val Leu Val
        115                 120                 125

Ala Gly Pro Asn Ser Tyr Lys Glu Ile Ile Leu Asn Ala His Glu Glu
    130                 135                 140

Glu His His Glu Ser Thr Trp Pro Asn Pro Tyr Pro Tyr Ser Lys Arg
145                 150                 155                 160

Met Ala Glu Lys Ala Val Leu Ala Thr Asn Gly Arg Leu Leu Lys Asn
                165                 170                 175

Gly Gly Thr Leu His Thr Cys Ala Leu Arg Leu Pro Phe Ile Tyr Gly
            180                 185                 190

Glu Glu Cys Gln Val Thr Ser Thr Val Lys Thr Ala Leu Lys Asn
        195                 200                 205

Asn Ser Ile Ile Lys Lys Asn Ala Thr Phe Ser Ile Ala Asn Pro Val
210                 215                 220

Tyr Val Gly Asn Ala Ala Trp Ala His Ile Leu Ala Ala Arg Ser Leu
225                 230                 235                 240

Gln Asp Pro Lys Lys Ser Pro Ser Ile Gln Gly Gln Phe Tyr Tyr Ile
                245                 250                 255

Ser Asp Asn Thr Pro His Gln Ser Tyr Asp Leu Asn Tyr Thr Leu
            260                 265                 270

Ser Lys Glu Trp Gly Leu Cys Leu Asp Ser Gly Trp Arg Leu Pro Leu
        275                 280                 285

Ser Leu Leu Tyr Trp Leu Ala Phe Leu Leu Glu Thr Val Ser Phe Leu
    290                 295                 300

Leu Arg Pro Val Tyr Asn Tyr Arg Pro Pro Phe Thr Arg Leu Leu Ile
305                 310                 315                 320

Thr Val Leu Asn Ser Val Phe Thr Ile Ser Tyr Lys Lys Ala Gln Arg
                325                 330                 335

Asp Leu Gly Tyr Gln Pro Leu Val Ser Trp Glu Glu Ala Lys Gln Lys
            340                 345                 350

Thr Ser Glu Trp Ile Gly Thr Leu Val Lys Gln His Arg Glu Thr Leu
        355                 360                 365

His Lys Lys Ser Gln
    370

<210> SEQ ID NO 4
<211> LENGTH: 334
<212> TYPE: PRT
<213> ORGANISM: Mus musculus

<400> SEQUENCE: 4

Met Arg Lys Val Val Leu Ile Thr Gly Ala Ser Ser Gly Ile Gly Leu
1                   5                   10                  15

Ala Leu Cys Gly Arg Leu Leu Ala Glu Asp Asp Leu His Leu Cys
                20                  25                  30

Leu Ala Cys Arg Asn Leu Ser Lys Ala Arg Ala Val Arg Asp Thr Leu
            35                  40                  45

Leu Ala Ser His Pro Ser Ala Glu Val Ser Ile Val Gln Met Asp Val
        50                  55                  60
```

-continued

```
Ser Ser Leu Gln Ser Val Val Arg Gly Ala Glu Glu Val Lys Gln Lys
 65                  70                  75                  80

Phe Gln Arg Leu Asp Tyr Leu Tyr Leu Asn Ala Gly Ile Leu Pro Asn
                 85                  90                  95

Pro Gln Phe Asn Leu Lys Ala Phe Phe Cys Gly Ile Phe Ser Arg Asn
            100                 105                 110

Val Ile His Met Phe Thr Thr Ala Glu Gly Ile Leu Thr Gln Asn Asp
            115                 120                 125

Ser Val Thr Ala Asp Gly Leu Gln Glu Val Phe Glu Thr Asn Leu Phe
130                 135                 140

Gly His Phe Ile Leu Ile Arg Glu Leu Glu Pro Leu Leu Cys His Ala
145                 150                 155                 160

Asp Asn Pro Ser Gln Leu Ile Trp Thr Ser Ser Arg Asn Ala Lys Lys
                165                 170                 175

Ala Asn Phe Ser Leu Glu Asp Ile Gln His Ser Lys Gly Pro Glu Pro
                180                 185                 190

Tyr Ser Ser Ser Lys Tyr Ala Thr Asp Leu Leu Asn Val Ala Leu Asn
            195                 200                 205

Arg Asn Phe Asn Gln Lys Gly Leu Tyr Ser Ser Val Met Cys Pro Gly
210                 215                 220

Val Val Met Thr Asn Met Thr Tyr Gly Ile Leu Pro Pro Phe Ile Trp
225                 230                 235                 240

Thr Leu Leu Leu Pro Ile Met Trp Leu Leu Arg Phe Phe Val Asn Ala
                245                 250                 255

Leu Thr Val Thr Pro Tyr Asn Gly Ala Glu Ala Leu Val Trp Leu Phe
                260                 265                 270

His Gln Lys Pro Glu Ser Leu Asn Pro Leu Thr Lys Tyr Ala Ser Ala
            275                 280                 285

Thr Ser Gly Phe Gly Thr Asn Tyr Val Thr Gly Gln Lys Met Asp Ile
            290                 295                 300

Asp Glu Asp Thr Ala Glu Lys Phe Tyr Glu Val Leu Leu Glu Leu Glu
305                 310                 315                 320

Lys Arg Val Arg Thr Thr Val Gln Lys Ser Asp His Pro Ser
                325                 330
```